United States Patent
I et al.

(10) Patent No.: US 9,739,855 B2
(45) Date of Patent: Aug. 22, 2017

(54) MAGNETIC RESONANCE IMAGING APPARATUS AND CONTROL METHOD FOR THE SAME

(71) Applicant: Samsung Electronics Co., Ltd., Gyeonggi-do (KR)

(72) Inventors: Gi Tae I, Gyeonggi-do (KR); Whoe Sun Yang, Gyeonggi-do (KR); Hye Jeong Lee, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 910 days.

(21) Appl. No.: 13/964,541

(22) Filed: Aug. 12, 2013

(65) Prior Publication Data
US 2014/0055133 A1  Feb. 27, 2014

(30) Foreign Application Priority Data
Aug. 22, 2012  (KR) .......................... 10-2012-0091700

(51) Int. Cl.
*G01V 3/00* (2006.01)
*G01R 33/48* (2006.01)
(Continued)

(52) U.S. Cl.
CPC ............ *G01R 33/48* (2013.01); *A61B 5/055* (2013.01); *A61B 5/1128* (2013.01); *A61B 5/1176* (2013.01); *A61B 5/165* (2013.01); *A61M 21/00* (2013.01); *G01R 33/28* (2013.01); *A61B 2576/026* (2013.01); *A61M 2021/0044* (2013.01); *A61M 2230/005* (2013.01); *G01R 33/283* (2013.01); *G01R 33/288* (2013.01); *G01R 33/56341* (2013.01)

(58) Field of Classification Search
CPC .. A61B 5/055; G01R 33/4828; G01R 33/543; G01R 33/5608
USPC ......................................................... 324/309
See application file for complete search history.

(56) References Cited

U.S. PATENT DOCUMENTS 5,355,885 A * 10/1994 Tsuda ..................... G01R 33/28
                                                            324/309
6,690,351 B1 * 2/2004 Wong ...................... G06F 1/163
                                                            345/156
(Continued)

FOREIGN PATENT DOCUMENTS

CN    1550207 A    12/2004
CN    101133968 A   3/2008
(Continued)

OTHER PUBLICATIONS

Chinese Search Report dated Feb. 4, 2017.
European Search Report dated Jan. 27, 2017.

*Primary Examiner* — Walter L Lindsay, Jr.
*Assistant Examiner* — Frederick Wenderoth
(74) *Attorney, Agent, or Firm* — Cha & Reiter, LLC

(57) ABSTRACT

A magnetic resonance imaging system adaptively and dynamically adjusts color and brightness of illuminators mounted on the inside of a bore in response to a scan sequence used for magnetic resonance imaging or the state of a patient in order to relieve discomfort during magnetic resonance imaging. An illuminator control unit selects and determines optical characteristics of the illuminators in response to a scan sequence or the state of a patient.

35 Claims, 22 Drawing Sheets

(51) Int. Cl.
*A61B 5/055* (2006.01)
*G01R 33/28* (2006.01)
*A61B 5/16* (2006.01)
*A61B 5/11* (2006.01)
*A61B 5/1171* (2016.01)
*G01R 33/563* (2006.01)
*A61M 21/00* (2006.01)

(56) References Cited

U.S. PATENT DOCUMENTS

| | | |
|---|---|---|
| 2005/0004444 A1 | 1/2005 | Boninger et al. |
| 2005/0199783 A1* | 9/2005 | Wenstrand ............ G06F 1/3203 250/214.1 |
| 2007/0126424 A1* | 6/2007 | Bittner ............... G01R 33/3804 324/307 |
| 2008/0055684 A1 | 3/2008 | Li |
| 2008/0204017 A1 | 8/2008 | Takamori et al. |
| 2008/0298054 A1 | 12/2008 | Paulussen et al. |
| 2009/0262551 A1 | 10/2009 | Trowell et al. |
| 2011/0214153 A1* | 9/2011 | Rosenfeld ................ H04N 7/15 725/78 |
| 2012/0143040 A1 | 6/2012 | Goswami et al. |
| 2012/0188354 A1* | 7/2012 | Munro ................... H04N 5/332 348/77 |

FOREIGN PATENT DOCUMENTS

| | | |
|---|---|---|
| CN | 101185572 A | 5/2008 |
| CN | 101326399 A | 12/2008 |
| CN | 101501520 A | 8/2009 |
| JP | 2010-124942 A | 6/2010 |
| JP | 2010-252970 A | 11/2010 |

* cited by examiner

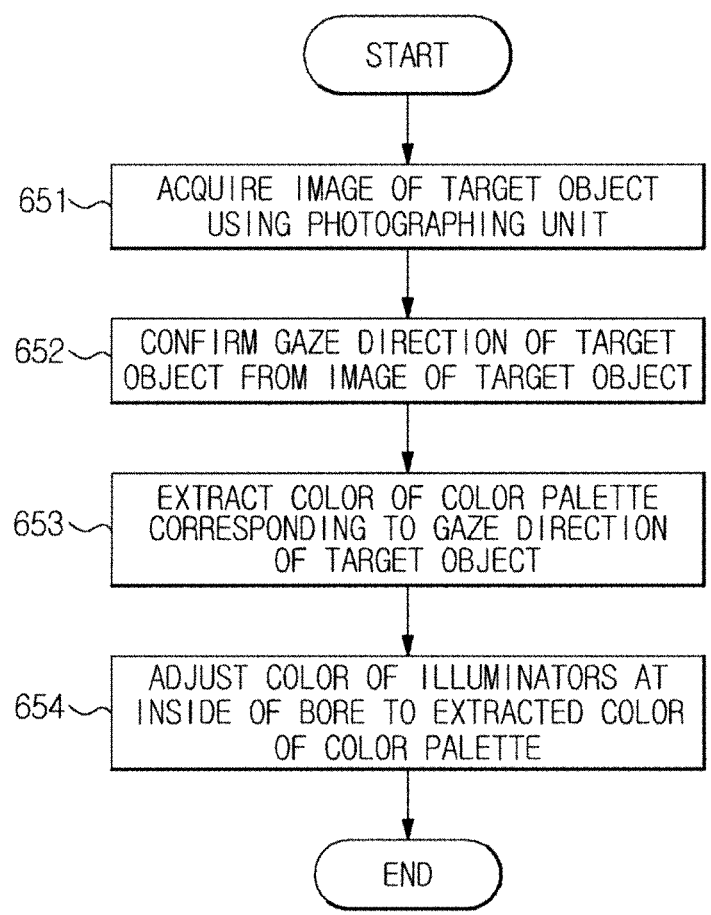

MAGNETIC RESONANCE IMAGING APPARATUS AND CONTROL METHOD FOR THE SAME

CROSS-REFERENCE TO RELATED APPLICATION

This application claims the benefit of Korean Patent Application No. 2012-0091700, filed on Aug. 22, 2012 in the Korean Intellectual Property Office, the disclosure of which is incorporated herein by reference.

FIELD OF THE INVENTION

This invention concerns a magnetic resonance imaging system and associated illumination controllable during magnetic resonance imaging for medical applications.

BACKGROUND

Medical imaging systems include an ultrasonic diagnostic apparatus, an X-ray tomographic apparatus, a magnetic resonance imaging apparatus and a medical diagnostic apparatus. These systems acquire information of a patient and provide an image. A magnetic resonance imaging apparatus has relatively free imaging conditions and provides excellent luminance contrast distinguishing soft tissue types and providing various diagnostic information valuable for diagnosis.

Magnetic resonance imaging (MRI) signal data is acquired based on density and physiochemical characteristics of atomic nuclei in response to nuclear magnetic resonance of hydrogen atoms in a human body using a magnetic field, which is not harmful to the human body in any way, and radio waves which are a non-ionizing form of radiation.

Specifically, a magnetic resonance imaging apparatus acquires images enabling diagnosis of the inside of a human body by converting energy discharged from atomic nuclei into a signal by supplying a designated frequency and energy to the atomic nuclei in a state in which a designated magnetic field is applied to the atomic nuclei.

In order to perform magnetic resonance imaging, a target object (e.g. a patient) is placed in a bore of a magnet assembly in a designated pose until magnetic resonance imaging is completed. Since the inner space of the bore maybe narrow and noise is generated from a magnet assembly during magnetic resonance imaging, the patient may feel discomfort and have difficulty holding the designated pose impairing acquisition and magnetic resonance image quality. A system according to invention principles addresses these deficiencies and related problems

SUMMARY

A magnetic resonance imaging system according to invention principles provides illumination inside of a bore with the illumination adjusted in color and brightness in response to magnetic resonance imaging sequence and/or the state of a patient in order to reduce patient discomfort during imaging. A magnetic resonance imaging apparatus comprises a magnet assembly and a bore for accommodating a patient. An illuminator unit is installed on the inside of the bore and an illuminator control unit controls optical characteristics of illuminators comprised in the illuminator unit in response to a scan sequence employed in magnetic resonance imaging.

Further, if the scan sequence is a scan sequence requiring a long time for magnetic resonance imaging, the illuminator control unit adjusts the color of the illuminators to a color associated with a short recognition time and if the scan sequence is a scan sequence sensitive to movement of a patient, the illuminator control unit adjusts the color of the illuminators to a color providing stability to the patient. The apparatus in an embodiment, includes a storage unit in which information regarding optical characteristics of the illuminators corresponding to scan sequences is stored and the illuminator control unit controls the optical characteristics of the illuminators using the information stored in the storage unit.

In a feature of the invention the magnetic resonance imaging apparatus comprises a photographing unit configured for acquiring an image of a patient in the bore; an illuminator unit installed on the inside of the bore; and an illuminator control unit determining a state of the by analyzing the image acquired by the photographing unit, and controlling optical characteristics of the illuminators comprised in the illuminator unit in response to the state of the patient. The image of the patient is a moving image or a still image photographed at a designated time interval and the photographing unit includes a wide viewing angle camera, and photographs a top view image of an inside of the bore. The illuminator control unit determines whether or not the patient moves by analyzing a plurality of acquired images and the illuminator control unit adjusts the color of the illuminators to a color supporting patient stability, upon determining that the patient moves.

An illuminator control unit varies the color of the illuminators according to degrees of movement of the patient. A storage unit stores data associating colors of the illuminators with corresponding degrees of movement of the patient and the illuminator control unit controls the color of the illuminators using the information stored in the storage unit. Further, the illuminator control unit recognizes pupils of the patient from the acquired image and compares a current pupil size of the patient with a pupil size of the patient at the initial stage of magnetic resonance imaging acquired images. If the current pupil size of the patient is greater than the pupil size of the patient at the initial stage of magnetic resonance imaging, the illuminator control unit adjusts the color of the illuminators to a color providing stability to the patient. If the pupils of the patient are not recognized as normal from the acquired image, the illuminator control unit adjusts the color of the illuminators to a color representing a short recognition time and increases brightness of the illuminators.

The illuminator control unit also recognizes a facial expression of the patient from the acquired image and adjusts the color of the illuminators to a color corresponding to a recognized facial expression of the patient. The illuminator control unit also determines a gaze direction of the patient from the acquired image and decreases brightness of illuminators corresponding to the determined gaze direction.

In a feature of the invention, a color palette comprising a plurality of arranged colors is installed on the inside of the bore and the illuminator control unit determines a gaze direction of the patient by analyzing the acquired image, and adjusts the color of the illuminators to a color of the color palette corresponding to the gaze direction of the patient. A storage unit stores information associating colors of the color palette with corresponding gaze directions of the patient and the illuminator control unit controls the color of the illuminators using the information stored in the storage unit.

A method of controlling a magnetic resonance imaging apparatus comprising a magnet assembly and a bore for accommodating a patient including illuminators installed on the inside of a bore, includes determining a scan sequence employed in magnetic resonance imaging. The method extracts optical characteristics corresponding to the scan sequence from a database provided in the magnetic resonance imaging apparatus, the optical; and controls the illuminators in response to the extracted optical characteristics. The method stores data in the database associating an illuminator color representing a short recognition time with a corresponding scan sequence requiring a long time for magnetic resonance imaging. The database associates a color providing stability to a patient with a corresponding scan sequence sensitive to movement of the patient.

In a further feature, the method acquires an image of a patient in the bore; determines the state of the patient by analyzing the acquired image; and controls optical characteristics of the illuminators in response to the state of the patient. The method also determines the state of the patient by determining whether or not the patient moves and the method adjusts the color of the illuminators to a color providing stability to the patient, upon determining that the patient moves. Further, judging of the state of the patient includes determining whether or not pupils of the patient are recognized from the acquired image or whether or not the pupils of the patient are dilated from the acquired image. If the pupils of the patient are not recognized, the method adjusts the color of the illuminators to a color representing a short recognition time and increases brightness of the illuminators. If the pupils of the patient are dilated, the method adjusts the color of the illuminators to a color providing stability to the patient.

The method judges the state of the patient by determining a gaze direction of the patient decreases brightness of illuminators corresponding to the determined gaze direction. The method also judges the state of the patient by determining which color a patient is looking at of a plurality of colors arranged on a color palette and adjusts the color of the illuminators to the color of the color palette at which a patient gazes.

BRIEF DESCRIPTION OF THE DRAWINGS

The features of the invention will become apparent and more readily appreciated from the following description of the embodiments, taken in conjunction with the accompanying drawings of which:

FIG. 19 is a flowchart illustrating a control method of a magnetic resonance imaging apparatus in accordance with principles of the present invention.

DETAILED DESCRIPTION

Figure 1:
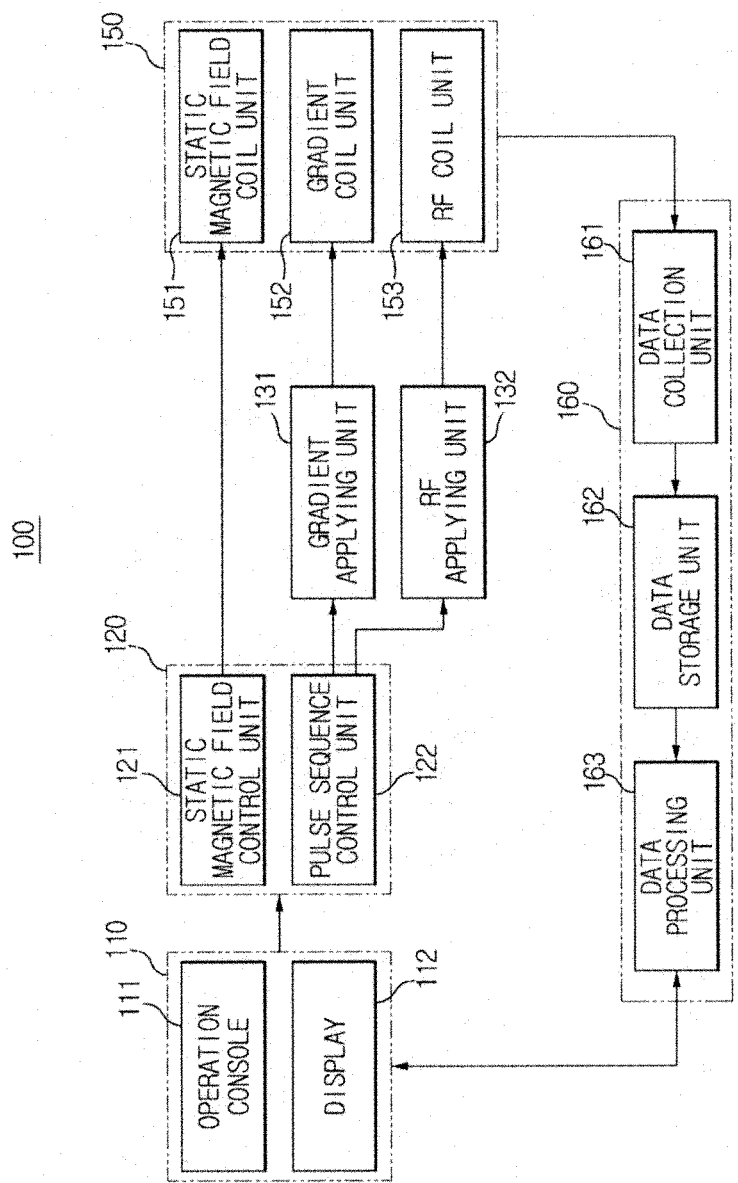
FIG. 1 is a control block diagram of a magnetic resonance imaging apparatus in accordance with principles of the present invention.

Reference will now be made in detail to the embodiments of the present invention, examples of which are illustrated in the accompanying drawings, wherein like reference numerals refer to like elements throughout.

FIG. 1 is a control block diagram of a magnetic resonance imaging apparatus including a magnet assembly 150 forming a magnetic field and generating resonance of atomic nuclei, a main control unit 120 controlling the operation of the magnet assembly 150, and an image processing unit 160 receiving an echo signal generated from the atomic nuclei and generating a magnetic resonance image. The magnet assembly 150 includes a static magnetic field coil unit 151 forming a static magnetic field, a gradient coil unit 152 forming gradient magnetic fields, and an RF coil unit 153 exciting the atomic nuclei by applying an RF pulse and receiving an echo signal from the atomic nuclei. The main control unit 120 includes a static magnetic field control unit 121 controlling the intensity and direction of the static magnetic field formed by the static magnetic field coil unit 151, and a pulse sequence control unit 122 determining a pulse sequence and controlling the gradient coil unit 152 and the RF coil unit 153.

The magnetic resonance imaging apparatus 100 includes a magnetic field gradient generation unit 131 applying a gradient signal to the gradient coil unit 152 and an RF unit 132 applying an RF signal to the RF coil unit 153, enabling the pulse sequence control unit 122 to control the gradient unit 131 and the RF unit 132 to adjust the gradient magnetic fields formed in the static magnetic field and the RF applied to the atomic nuclei. Further, user operation unit 110 receives control instructions regarding the overall operation of the magnetic resonance imaging apparatus 100 from a user including instructions regarding a sequence from the user and in response unit 100 generates a pulse sequence. The user operation unit 110 includes an operation console 111 enabling a user to operate a system, and a display 112 displaying data indicating a control state and displaying an image generated by the image processing unit 160 for diagnosis of a patient condition.

Figure 2:
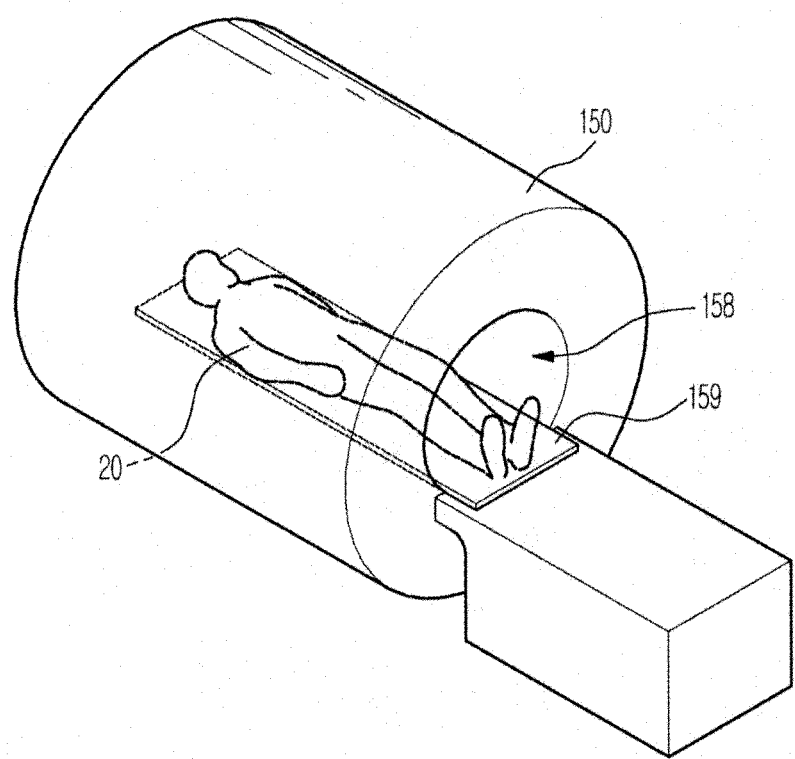
FIG. 2 is a perspective view schematically illustrating the external appearance of the magnetic resonance imaging apparatus in accordance with principles of the present invention.
Figure 3:
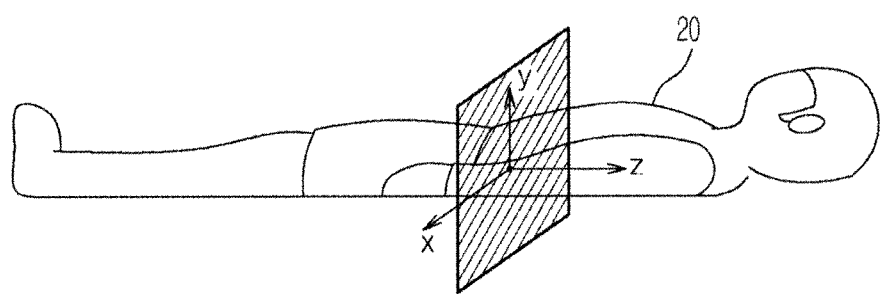
FIG. 3 is a view illustrating division of a space in which a target object is placed, by the X-axis, Y-axis and Z-axis in accordance with principles of the present invention.
Figure 4:
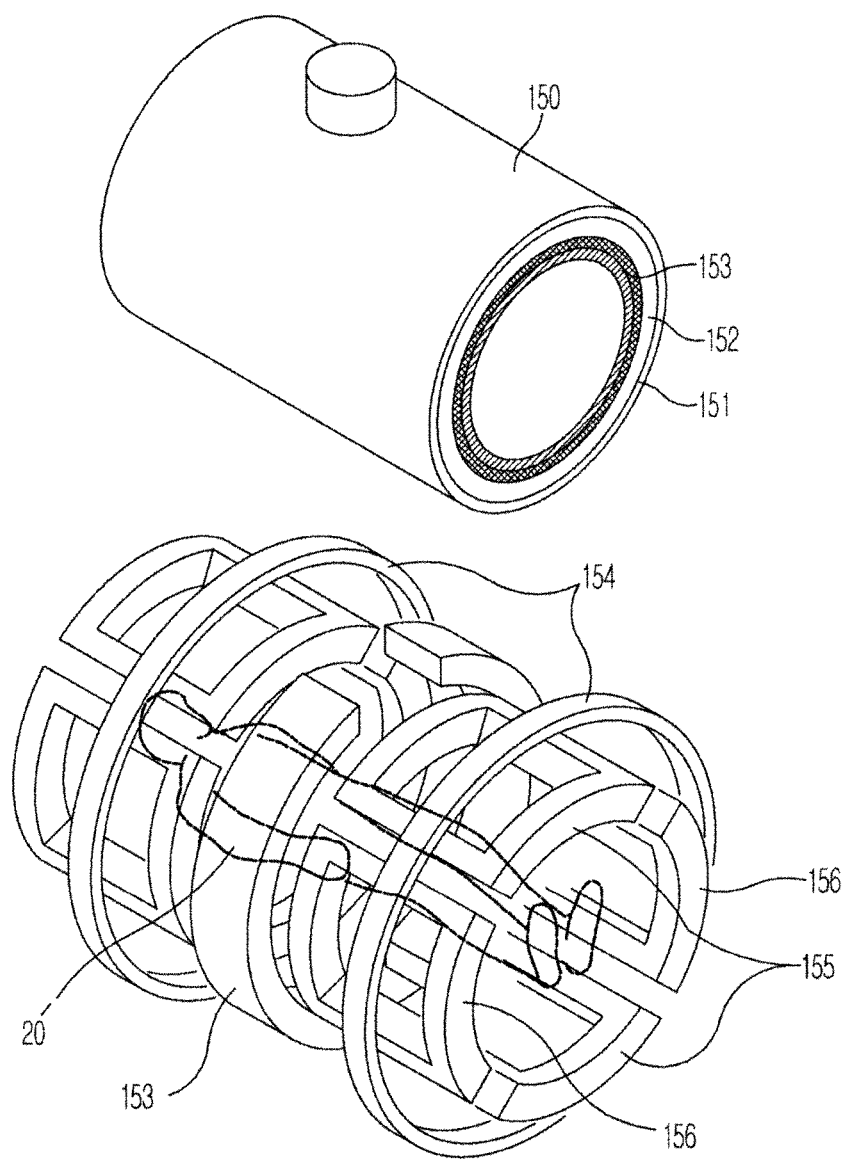
FIG. 4 is a view illustrating the structure of a magnet assembly and the structure of a gradient coil unit in accordance with principles of the present invention.
Figure 5:
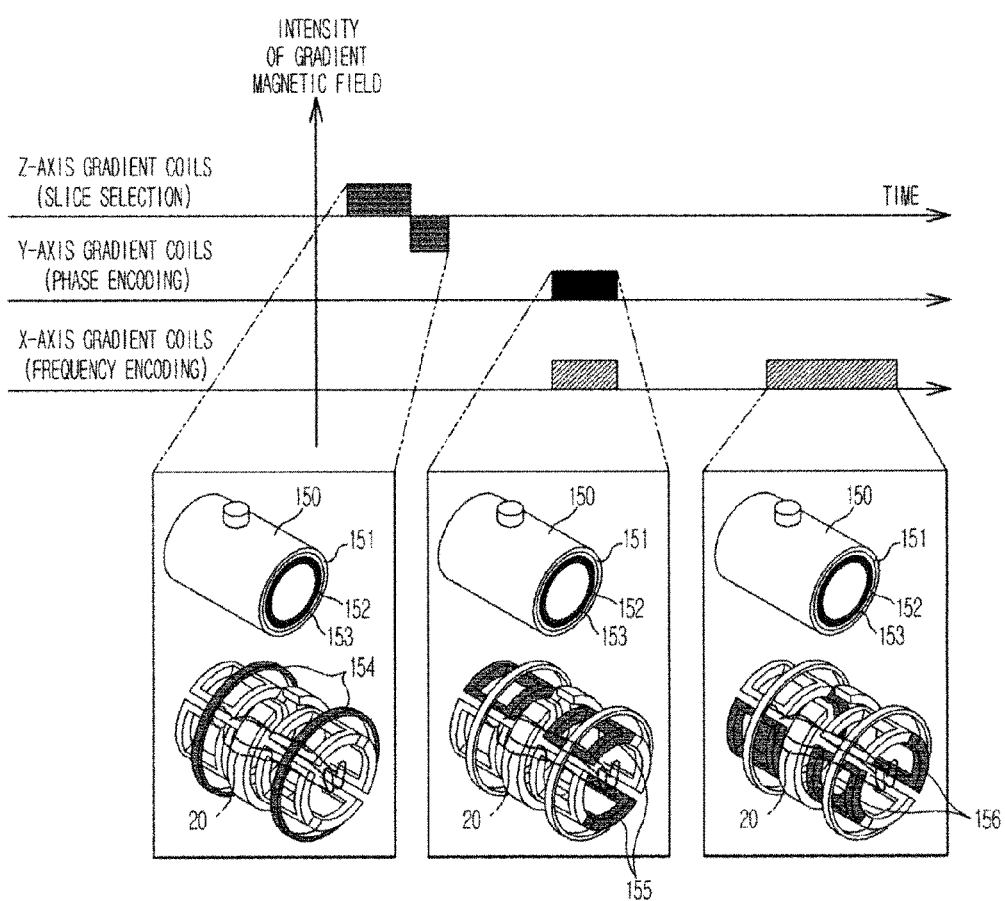
FIG. 5 is a view illustrating respective gradient coils constituting the gradient coil unit and a pulse sequence regarding the operation of the respective gradient coils in accordance with principles of the present invention.

FIG. 2 is a perspective view schematically illustrating the external appearance of the magnetic resonance imaging apparatus, FIG. 3 is a view illustrating division of a space in which a target object is placed, by the X-axis, Y-axis and Z-axis, FIG. 4 is a view illustrating the structure of the magnet assembly and the structure of the gradient coil unit, and FIG. 5 is a view illustrating respective gradient coils comprising the gradient coil unit and a pulse sequence regarding the operation of the respective gradient coils. The magnet assembly 150 has a cylindrical shape, the inner space of which is vacant, and such an inner space is referred to as a cavity or a bore 158. When a target object 20 lays on a patient table 159, the magnetic resonance imaging apparatus 100 transfers the patient table 159 into the bore 158 so that the target object 20 laying on the patient table 159 is located at an imaging position. The static magnetic field coil unit 151 may be formed in a shape in which a coil is wound around the bore 158, and when current is applied to the static magnetic field coil unit 151, a static magnetic field is formed at the inside of the magnet assembly 150 in the bore 158. The direction of the static magnetic field is typically parallel with the axis of the magnet assembly 150.

In response to a static magnetic field being provided in the bore 158, atomic nuclei of atoms of the target object 20, particularly, hydrogen atoms, are arranged in the direction of the static magnetic field and precess in the direction of the static magnetic field. The precession speed of atomic nuclei may be represented as a precession frequency referred to as a Larmor frequency and expressed by Equation 1 below.

$$\omega = \gamma B_0 \quad \text{[Equation 1]}$$

Here, $\omega$ is a Larmor frequency, $\gamma$ is a proportional constant, and $B_0$ is the intensity of an external magnetic field. The proportional constant varies according to type of atomic nuclei, the unit of the intensity of the external magnetic field is tesla (T) or gauss (G), and the unit of the precession frequency is Hz. For example, hydrogen protons have a procession frequency of 42.58 MHz, in the external magnetic field of 1T and, among elements constituting a human body, hydrogen occupies the largest percentage, and thus a magnetic resonance signal is acquired predominantly in response to precession of hydrogen protons during MRI. The gradient coil unit 152 generates magnetic field gradients in the bore 158.

As shown in FIG. 3, an axis running parallel with the lengthwise direction from the head to the feet of the target object 20, i.e., an axis running parallel with the direction of the static magnetic field, is defined as the Z-axis, an axis running parallel with the lateral direction of the target object 20 is defined as the X-axis, and an axis running parallel with the vertical direction in the space is defined as the Y-axis. In order to acquire 3D spatial information, gradient magnetic fields in all directions of the X-axis, Y-axis and Z-axis are required. Therefore, the gradient coil unit 152 includes 3 pairs of gradient coils.

As shown in FIGS. 4 and 5, Z-axis gradient coils 154 include a pair of ring type coils, and Y-axis gradient coils 155 are located above and below the target object 20. X-axis gradient coils 156 are located at the left and right sides of the target object 20. When direct currents having opposite polarities flow in the two Z-axis gradient coils 154 in opposite directions, the magnetic field is changed in the Z-axis direction and thus a gradient magnetic field is formed. FIG. 5 illustrates formation of the Z-axis gradient magnetic field during operation of the Z-axis gradient coils 154 through a pulse sequence. As the gradient of the gradient magnetic field formed in the Z-axis increases, a slice having a smaller thickness may be selected. Therefore, the Z-axis gradient coils 154 are used to select a slice. Spins constituting the slice have the same frequency and the same phase and thus the respective spins are indistinguishable. In response to a gradient magnetic field in the Y-axis direction being formed by the Y-axis gradient coils 155, the gradient magnetic field causes phase shift so that rows of the slice have different phases. The phase of the spins of the row to which a relatively large gradient magnetic field is applied correspond to a higher frequency, and the phase of the spins of the row to which a relatively small gradient magnetic field is applied correspond to a lower frequency. Phase shift of the respective rows of the selected slice occurs in response to the Y-axis gradient magnetic field being removed and thus the rows have different phases enabling individual rows to be distinguished from one another and identified. The gradient magnetic field formed by the Y-axis gradient coils 155 is used in phase encoding in response to a pulse sequence as illustrated in FIG. 5.

The slice is selected through the gradient magnetic field formed by the Z-axis gradient coils 154, and the rows comprising the selected slice are distinguished from one another by different phases. However, the respective spins constituting each row have the same frequency and the same phase, and are thus indistinguishable. In response to a gradient magnetic field in the X-axis direction being formed by the X-axis gradient coils 154, the gradient magnetic field causes the spins comprising each row to have different frequencies so that the respective spin rows are distinguishable from one another. Further, the X-axis gradient magnetic field formed by gradient coils 156 is used for frequency encoding.

The gradient magnetic fields formed by the Z-axis, Y-axis and X-axis gradient coils provide encoding of spatial positions of the respective proton spins, i.e., spatial encoding, through slice selection, phase encoding and frequency encoding. The gradient coil unit 152 is connected to the gradient unit 131 which applies a drive signal to the gradient coil unit 152 in response to a control signal transmitted from the pulse sequence control unit 122 for generating gradient magnetic fields. The gradient unit 131 includes three drive circuits corresponding to the three pairs of gradient coils 154, 155 and 156 of the gradient coil unit 152.

Lorentz force is generated when current is applied to the gradient coil unit 152 in order to generate gradient magnetic fields. Such Lorentz force causes vibration of the coils, and such vibration causes noise generated during magnetic resonance imaging. A noise level varies according to shapes and sizes of the gradient magnetic fields through imaging techniques, and relates to characteristics of gradient magnetic field coils. The atomic nuclei arranged by an external magnetic field precess at the Larmor frequency and the magnetization vector sum of multiple atomic nuclei is represented as net magnetization M. Measurement of a Z-axis component of the net magnetization M may not be impossible, and thus only $M_{xy}$ is detected. Therefore, in order to acquire a magnetic resonance signal, the net magnetization needs to be present on the X-Y plane through excitation of the atomic nuclei. In order to excite the atomic nuclei, an RF pulse tuned to the Larmor frequency of the atomic nuclei is applied. The RF coil unit 153 includes a transmission coil transmitting an RF pulse, and a reception coil receiving electromagnetic waves emitted from the excited atomic nuclei, i.e., a magnetic resonance signal.

The RF coil unit 153 is connected to the RF unit 132 which applies a drive signal to the RF coil unit 153 in response to a control signal transmitted from the pulse sequence control unit 122. The RF unit 132 includes a modulation circuit modulating a high frequency output signal to provide a pulse type signal, and an RF power amplifier amplifying the pulse type signal. Further, the RF coil unit 153 is connected to the image processing unit 160, and the image processing unit 160 includes a data collection unit 161 receiving data regarding the magnetic resonance signal generated from the atomic nuclei and a data processing unit 163 generating a magnetic resonance image by processing the data received by the data collection unit 161. The data collection unit 161 includes a pre-amplifier amplifying the magnetic resonance signal received by the reception coil of the RF coil unit 153, a phase detector receiving the magnetic resonance signal transmitted from the pre-amplifier and detecting a phase, and an ND converter converting an analog signal acquired through phase detection into a digital signal. Further, the data collection unit 161 transmits the magnetic resonance signal converted into the digital signal to a data storage unit 162.

Data storage unit 162 includes data space comprising a 2D Fourier space for storage of overall data acquired in response to scanning. The data processing unit 163 reconstructs an image of the target object 20 by performing a 2D inverse Fourier transform upon data in the 2D Fourier space and the reconstructed image is displayed on the display 112. As a method to acquire a magnetic resonance signal from atomic nuclei, a spin echo pulse sequence is generally used. If the RF coil unit 153 applies RF pulses, when an RF pulse is transmitted one more time by a proper time interval Δt after application of the first RF pulse, strong transverse magnetization of the atomic nuclei occurs after a time Δt, and a magnetic resonance signal is acquired from the transverse magnetization. This is referred to as a spin echo pulse sequence, and time taken to generate the magnetic resonance signal after application of the first RF pulse is referred to as time echo (TE).

A flip degree of protons comprises an angle to which the protons move from an axis and is represented as a 90 degree RF pulse, a 180 degree RF pulse, for example according to the flip degree of the protons. Magnetic resonance imaging typically takes more than 30 minutes, and in some cases may take more than 1 hour. In order to allow the magnetic resonance imaging apparatus to acquire a magnetic resonance image of a specific region of the target object through the above-described process, it is desirable that the target object hold a designated pose in the bore, as described above. However, if the target object, such as an elderly person, a first-aid patient, or a patient with a back alignment, holds a designated pose for a long time in the bore in which, on overage, noise of 65 to 95 dB occurs, the target object feels mental and physical discomfort which may result in patient movement and degraded image quality.

Figure 6A:
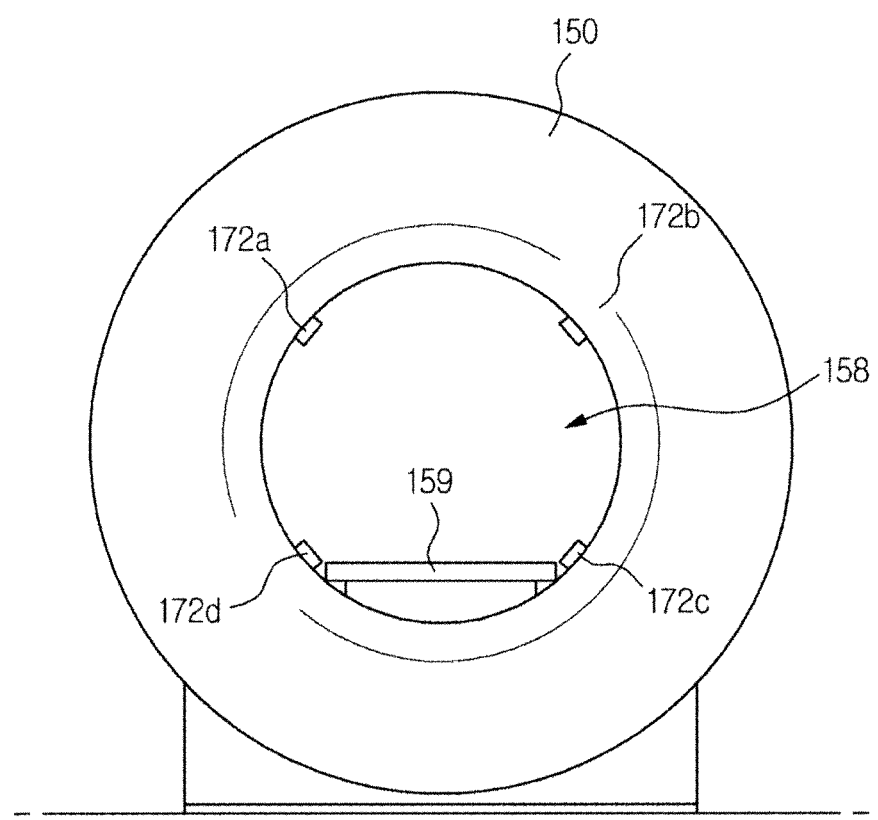
FIG. 6A is a view illustrating the external appearance of the magnet assembly in which illuminators are mounted, as seen from a position at which the head of a target object is placed in accordance with principles of the present invention.
Figure 6B:
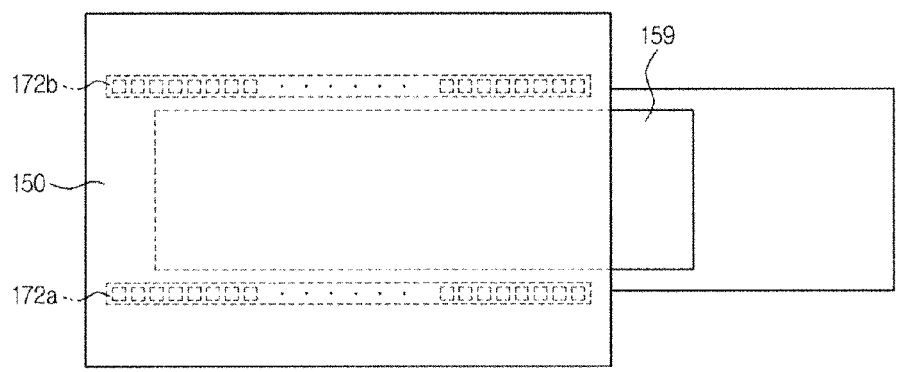
FIG. 6B is a view illustrating the external appearance of the magnet assembly in which the illuminators are mounted, as seen from the top in accordance with principles of the present invention.

In magnetic resonance imaging apparatus 100, inner illuminators are installed in the bore, and the color of the inner illuminators is advantageously adjusted in response to a sequence used in magnetic resonance imaging to enhance comfort of a patient. FIG. 6A is a view illustrating the external appearance of the magnet assembly in which illuminators are mounted, as seen from a position at which the head of a target object is placed, and FIG. 6B is a view illustrating the external appearance of the magnet assembly in which the illuminators are mounted, as seen from the top. Four illuminators 172a, 172b, 172c and 172d in FIG. 6A, are mounted in the bore 158 on the inner surface of the magnet assembly 150 to illuminate the overall inside of the bore 158, for example. The installed positions of the illuminators 172a, 172b, 172c and 172d are determined in response to desired radiation angle of light. Illuminators 172a, 172b (and 172c and 172d not shown) in FIG. 6B, are arranged in an array in a line. The illuminators 172a, 172b, 172c and 172d comprise light sources unaffected by high magnetic field conditions in the bore 158 such as LEDs. However, the number and structure of the illuminators shown in FIGS. 6A and 6B are exemplary only.

Figure 7:
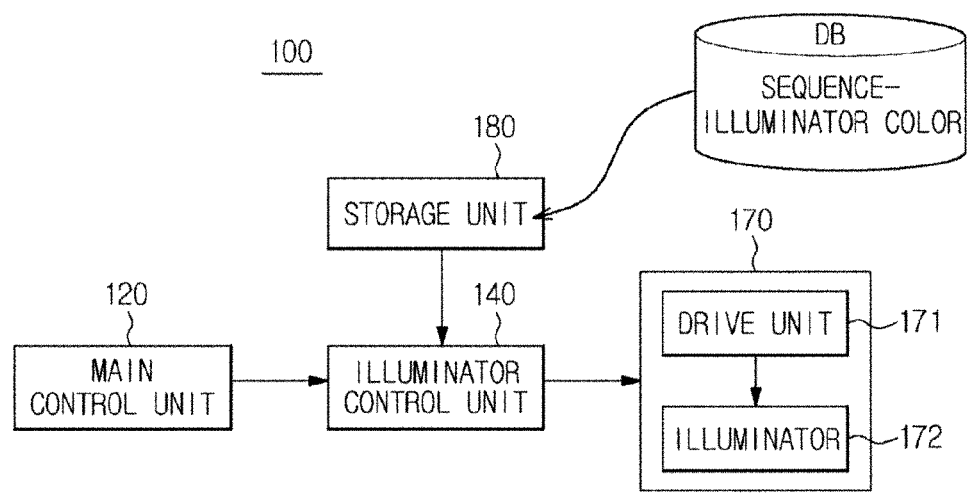
FIG. 7 is a control block diagram of the magnetic resonance imaging apparatus in which the illuminators are controllable in accordance with principles of the present invention.

FIG. 7 shows a control block diagram of the magnetic resonance imaging apparatus 100 in which the illuminators are controllable. The magnetic resonance imaging apparatus 100 includes an illuminator unit 170 installed within the bore 158, an illuminator control unit 140 controlling optical characteristics of the illuminator unit 170, and a storage unit 180 storing information regarding the optical characteristics of the illuminator unit 170. The optical characteristics of the illuminator unit 170 mean characteristics, such as color, brightness, illuminance and luminance of light emitted from the illuminator unit 170. The illuminator unit 170 includes the illuminators 172 shown in FIGS. 6A and 6B, and a drive unit 171 driving the illuminators 172. The optical characteristics comprising color or brightness of light of illuminators 172 are adjustable.

The illuminator control unit 140 varies the color of light emitted from the illuminators 172 in response to a scan sequence applied to magnetic resonance imaging unit 100. The scan sequence of the present invention represents a kind of an imaging method applied to the MRI scan. The storage unit 180 stores a database of information regarding illuminator colors associated with corresponding different respective scan sequences used in magnetic resonance imaging, and thus the illuminator control unit 140 receives information regarding the scan sequence applied to magnetic resonance imaging from the main control unit 120 and extracts an illuminator color corresponding to the scan sequence from the storage unit 180. The illuminator control unit 140 inputs a control signal to the illuminator unit 170 dynamically determining and adjusting color of the illuminators 172 in response to an associated scan sequence.

Figure 8:
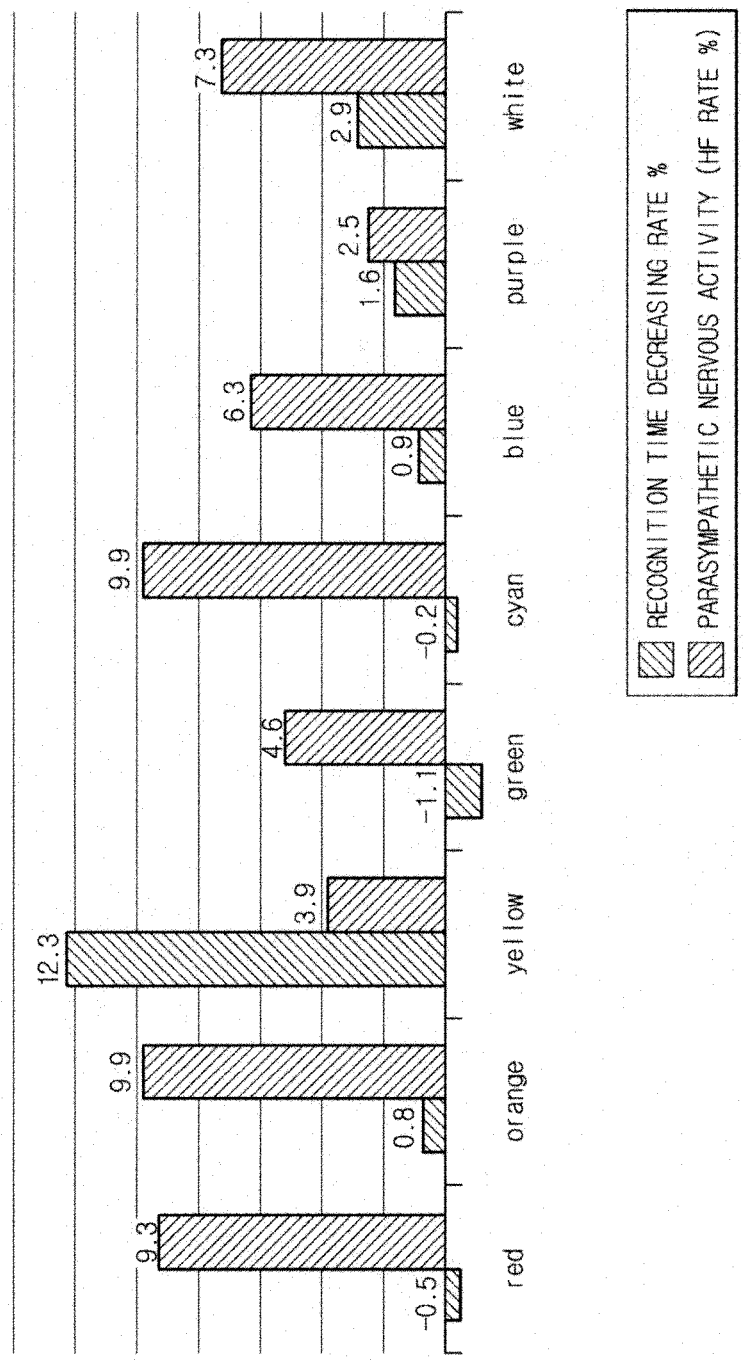
FIG. 8 is a graph representing variations of recognition time and stability of a human according to colors in accordance with principles of the present invention.

FIG. 8 shows an graph representing variation of human recognition time and recognition stability in response to colors change. Through known experimental results, human recognition time and stability vary according to color. Herein, recognition time is the time perceived by a human, not time which has actually elapsed, and long recognition time means that a human feels that time is moving slowly. Stability may be represented as an HF (heart frequency) rate indicating parasympathetic nervous activity in an R-R interval variability (RRV) measurement signal, and a higher HF rate means that a human feels stable. The recognition time decreasing rate (12.3%) of yellow is the highest, and the HF rate (9.9%) of orange and cyan is the highest. Therefore, a human feels that time is moving fast in yellow environments, and a human feels stable in orange or cyan environments.

The storage unit 180 stores information enabling illuminator control to provide illuminator color having a high recognition time decreasing rate corresponding to a scan sequence with long imaging time and a color having a high HF rate corresponding to a scan sequence sensitive to movement of a patient. However, the data of FIG. 8 is applicable to one embodiment, other experimental or statistical results are applicable to other embodiments. There are various kinds of the scan sequences employed for magnetic resonance imaging tailored to patient regions to be imaged, imaging methods, or for specific diagnosis purposes. These scan sequences include sequences for diffusion tensor imaging (DTI), MR spectroscopy (MRS), functional MRI (fMRI), and diffusion weighted imaging (DWS), for example.

DTI is an imaging method used to investigate the fine structure of biological tissues due to anisotropy in diffusion using the fact that diffusion degrees of water molecules vary according to structures of biological tissues, and is used to image neural cells to check for brain abnormalities. DTI imaging requires a relatively long performance time and a color having a high recognition time decrease rate (for example, yellow) corresponding to a DTI sequence.

MRS is an imaging method to analyze an electromagnetic wave signal, generated from specific atoms through a frequency region spectrum when a natural frequency (an RF pulse) exciting the specific atoms is momentarily applied to a target object placed in a magnetic field, by Fourier transform, and is used to quantitatively analyze the structure, components and state of a diagnostic region. The MRS imaging method is sensitive to movement of a patient. Therefore, a unit 100 provides a color having a high HF rate (for example, orange or cyan) corresponding to an MRS sequence.

fMRI is an imaging method used to detect variation of an inherent function of the cerebral cortex through an image. The fMRI imaging method determines the positions of brain functions prior to brain surgery and is used to determine a resection range and to predict damage due to surgery. fMRI imaging requires a long time to perform and is sensitive to movement of a target object. Therefore, a color having both a high HF rate and a high recognition time decreasing rate (for example, white) is used by unit 100 for an fMRI sequence. DWI is an imaging method based on the fact that, when a strong gradient magnetic field is applied to a material which is well diffused, phase shift of the material is severe and thus the material represents great signal reduction, and a material which is poorly diffused represents little signal reduction in a strong gradient magnetic field, and is used to diagnose acute cerebral infraction, brain tumors, and white matter-related diseases of the brain. DWI imaging is susceptible to motion artifacts as DWI imaging is sensitive to slight patient movement. Therefore, a color having a high HF rate (for example, yellow) is displayed by unit 100 for a DWI sequence. However, since imaging time and sensitivity to movement in application of each scan sequence varies due to types and advances in magnetic resonance imaging, a system map in unit 180 associating scan sequences and illuminator colors is dynamically changeable.

Further, in order to maximize illumination effects, the magnetic resonance imaging apparatus 100 in one embodiment controls illuminators on the outside of the bore 158 as well as illuminators on the inside of the bore 158. Here, the outer illuminators of the bore 158 mean illuminators of a scan room in which magnetic resonance imaging is carried out. Further, since the head of the target object 20 may protrude from the bore 158 according to regions to be imaged, only the outer illuminators of the bore 158 may be controlled in a particular application. The outer illuminators of the bore 158 may alternatively be controlled in the same manner as the inner illuminators of the bore 158.

Figure 9:
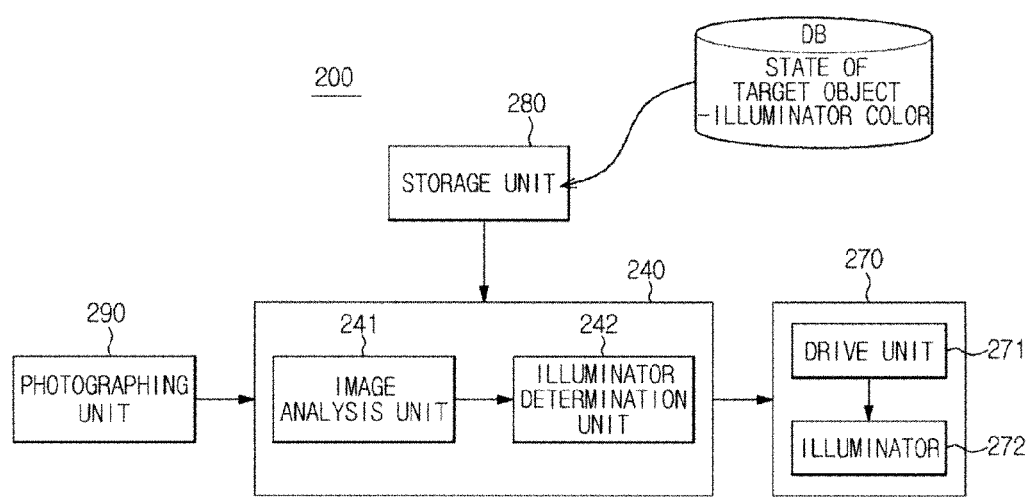
FIG. 9 is a control block diagram of a magnetic resonance imaging apparatus in accordance with principles of the present invention.

FIG. 9 shows a control block diagram of a magnetic resonance imaging apparatus 200 determining the state of a patient and adjusting illuminator color on the inside of the bore to suit the determined state including at least one of, movement of the patient, an eye pupil state of the patient and a facial expression of the patient. For this purpose, the magnetic resonance imaging apparatus 200 includes an illuminator unit 270, a photographing unit 290 photographing the image of the patient, a storage unit 280 storing information associating optical characteristics of illuminators with corresponding states of the patient, and an illuminator control unit 240 controlling the illuminator unit 270 using the photographed image of the patient and the information stored in the storage unit 280. The illuminator unit 270 includes illuminators 272 and a drive unit 271 in the same manner as the above-described embodiment, and the illuminators 272 may comprise LEDs unaffected by high magnetic field conditions. The photographing unit 290 acquires the image of a patient by photographing the patient occupying the inside of the bore. Hereinafter, with reference to FIGS. 10A and 10B together with FIG. 9, the structure and operation of the photographing unit 290 will be described in detail.

Figure 10A:
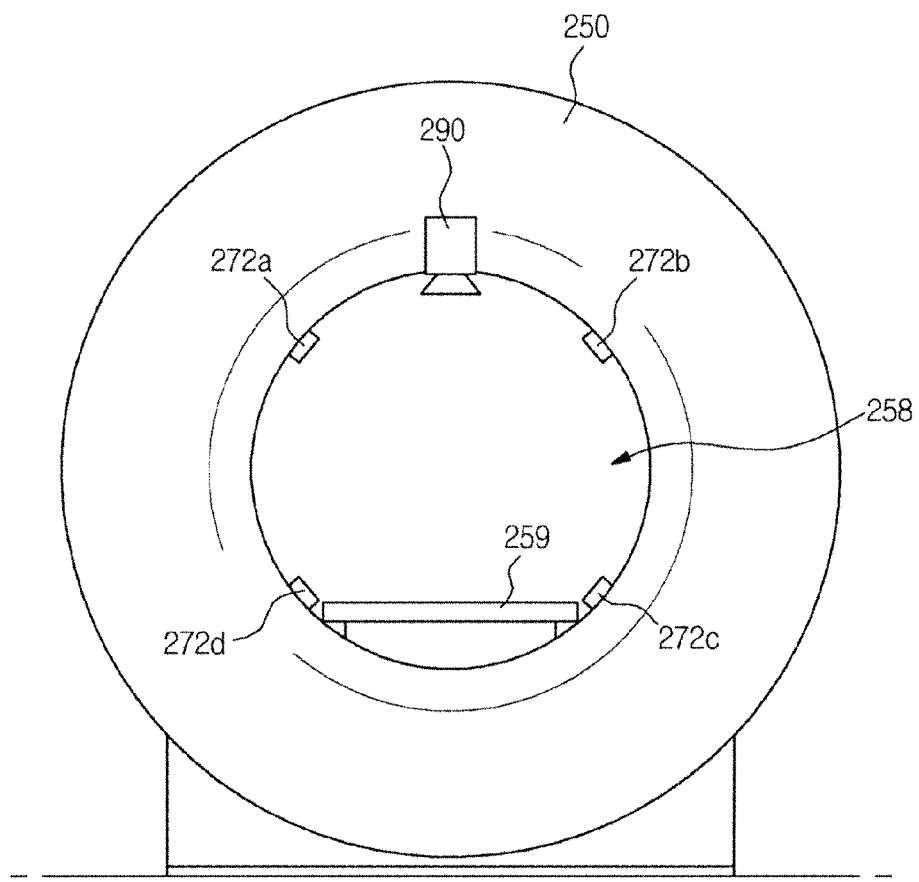
FIGS. 10A and 10B are views illustrating the external appearance of the magnetic resonance imaging apparatus in which a photographing unit is mounted in accordance with principles of the present invention.
Figure 10B:
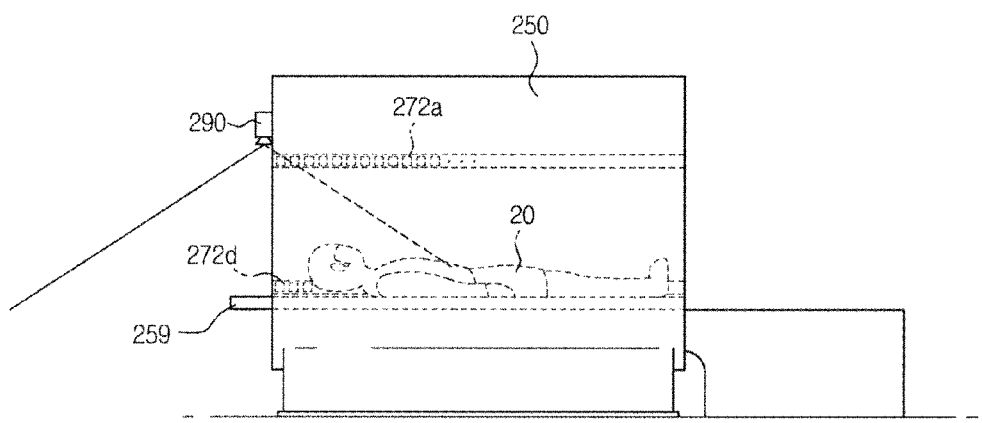

FIGS. 10A and 10B show views illustrating the external appearance of the magnetic resonance imaging apparatus in which the photographing unit is mounted. FIG. 10A shows a view illustrating the external appearance of the magnetic resonance imaging apparatus, as seen from a position at which the head of a patient is placed, and FIG. 10B shows a view illustrating the external appearance of the magnetic resonance imaging apparatus, as seen from the side. With reference to FIG. 10A, illuminators 272*a*, 272*b*, 272*c* and 122*d* (comprising four LED arrays) are installed on the inner surface of the magnet assembly 250 so as to illuminate the inside of the bore 258. The photographing unit 290 is installed on the outside of the bore 258 and is unaffected by a magnetic field formed in the bore 258. The photographing unit 290 is installed above the position at which the head of the patient transferred to the inside of the bore 258 is located, and photographs a top view image including the face of the patient.

With reference to FIG. 10B, the photographing unit 290 comprises a wide viewing angle camera. In order to detect movement of the patient or recognize the facial expression or the pupils of the patient, photographing of the inside of the bore 258 is required. However, the photographing unit 290 is installed at the outside of the bore 258 because of the magnetic field formed in the bore 258, and if the photographing unit 290 is a wide viewing angle camera having a wider viewing angle than a general camera, the photographing unit 290 located at the outside of the bore 258 may photograph the patient 20 located at the inside of the bore 258. The depth of the inside of the bore 258 which may be photographed varies according to viewing angles of the camera, and the viewing angle of the camera is determined using Equation 2 below.

$$m = h/\tan(180 - \alpha/2) \quad \text{[Equation 2]}$$

Here, m indicates the depth of the inside of the bore 258 which is photographed by the photographing unit 290, h indicates the height to the photographing unit 290 from the patient table 259, and a indicates α viewing angle. Here, it is assumed that the photographing unit 290 is installed at the end of the magnet assembly 250. For example, if the photographing unit 290 is a wide viewing angle camera having a viewing angle (α) of 114 degrees and the height (h) to the photographing unit 290 from the patient table 259 is about 40 cm, the inside of the bore 258 up to about 61.53 cm may be photographed based on Equation 2 above. The length of the magnet assembly of the general magnetic resonance imaging apparatus is about 120 cm, and thus it is understood that more than half of the inside of the bore 258 may be within a photographing range. Therefore, if a wide viewing angle camera having a viewing angle (α) of 114 degrees is used as the photographing unit 290, the photographing range of about 120 cm based on the end of the magnet assembly 250 is secured, and thus a face image or a movement image of the patient is stably acquired.

However, the viewing angle of the photographing unit 290 is not limited thereto, and the photographing unit 290 having viewing angles of various ranges according to lengths of the magnet assembly 250 may be used. With reference to FIG. 9, the illuminator control unit 240 includes an image analysis unit 241 analyzing an image acquired by the photographing unit 290, and an illuminator determination unit 242 determining an illuminator color using a result of image analysis of the image analysis unit 241 and the information stored in the storage unit 280.

The image analysis unit 241 determines the state of the patient by analyzing the image of the patient acquired by the photographing unit 290. The image acquired by the photographing unit 290 may be a still image photographed at a designated time interval or a moving image photographed in real time.

In accordance with one embodiment, the image analysis unit 241 determines whether or not the patient moves by analyzing the image of the patient. In more detail, the image photographed by the photographing unit 290 is transferred to the image analysis unit 241, and the image analysis unit 241 acquires an initial pose of the patient by extracting a region representing the shape of the patient from the image photographed at the beginning of magnetic resonance imaging. Then, the image analysis unit 241 acquires the current pose of the patient from the current image of the patient, compares the current pose with the initial pose of the patient, and transmits a result of comparison to the illuminator determination unit 242. A boundary detection method, as known, is used in analysis the pose of the patient and comparison between the current pose and initial pose of the patient. The image analysis method detects image object boundaries based on determination of object edges comprising linear pixel luminance transitions and matching with stored known template object (e.g. patient, pupil, face and facial expression) shapes.

The image analysis unit 241 recognizes eye pupils of the patient from the photographed image. In more detail, the photographing unit 290 acquire an image of the patient at the beginning of magnetic resonance imaging and transmits an acquired initial image to the image analysis unit 241. The image analysis unit 241 recognizes the pupils of the patient from the initial image of the patient, and calculates the size of the pupils. Then, when the photographing unit 290 photographs the patient in real time or at a designated time interval and transmits an acquired current image to the image analysis unit 241, the image analysis unit 241 compares the size of the pupils in the current image with the size of the pupils in the initial image of the patient, and transmits a result of comparison to the illuminator determination unit 242.

The image analysis unit 241 recognizes the facial expression of the patient from the photographed image using a facial expression recognition method. In more detail, the image analysis unit 241 extracts a facial region of the patient from the photographed image, and recognize the facial expression of the patient based on the positions of eyes, a nose and a mouth and matching with predetermined stored facial feature arrangements having a known expression. Any one of multiple known facial expression recognition methods are usable. For example, the image analysis unit 241 determines which stage, among plural facial expression stages express a degree of discomfort and transmits the detected expression to unit 242.

The illuminator determination unit 242 determines the color of illuminators based on the result of judgment of the image analysis unit 241. When the image analysis unit 241 judges that the patient moves in a particular recognized manner the color of illuminators is changed to a color providing stability to the patient (for example, orange or cyan). Further, the illuminator determination unit 242 determines the color of illuminators according to a degree of movement of the patient. The degree of movement of the patient is determined based on a difference between the initial pose and the current pose of the patient. For example, the illuminator determination unit 242 judges that a degree of discomfort of the patient is higher as the degree of movement of the patient is higher, and determines a color exhibiting higher parasympathetic nervous activity (a color providing stability) as the illuminator color. Information stored in the storage unit 280 is used, and thus, the storage unit 280 stores information regarding illuminator colors corresponding to degrees of movement of the patient.

Further, the image analysis unit 241 transmits the result of recognition of the state of the pupils of the patient to the illuminator determination unit 242 which determines the illuminator color in response to the state of the pupils. In more detail, if the image analysis unit 241 transmits a difference between the initial pupil size and the current pupil size of the patient to the illuminator determination unit 242, the illuminator determination unit 242 determines the illuminator color based on the difference. For example, the illuminator determination unit 242 judges that a degree of discomfort of the patient is higher as the size of the pupils of the patient expands, and determines a color exhibiting higher parasympathetic nervous activity (orange or cyan) as the illuminator color. Here, information stored in the storage unit 280 is used, and thus, the storage unit 280 stores information regarding illuminator colors corresponding to differences of pupil sizes of the patient.

If the pupils of the patient are not recognized or detected size change is below a designated reference size, the illuminator determination unit 242 judges that patient is in a sleeping state or in a drowsy state, and determines a color having a higher recognition time decreasing rate (yellow) as the illuminator color. Here, the illuminator determination unit 242 increases brightness of the illuminators and in conjunction changes color of the illuminators or just increases brightness of the illuminators without color change of the illuminators in order to awaken the patient. Further, when the image analysis unit 241 transmits the result of recognition of the facial expression of the patient to the illuminator determination unit 242, the illuminator determination unit 242 determines the illuminator color according to the received recognized facial expression. For example, the illuminator determination unit 242 judges that a degree of discomfort of the patient is higher as the facial expression of the patient recognized by the image analysis unit 241 corresponds to a facial expression stage expressing a higher degree of discomfort, and determines a color exhibiting higher parasympathetic nervous activity (orange or cyan) as the illuminator color. Information stored in the storage unit 280 associates illuminator colors with corresponding facial expressions of the patient.

Further, in order to maximize such effects, the magnetic resonance imaging apparatus 200 controls illuminators on the outside of the bore 258 as well as the illuminators on the inside of the bore 258. Here, the outer illuminators of the bore 258 means illuminators of a scan room in which magnetic resonance imaging is carried out. Further, since the head of the patient 20 may protrude from the bore 258, just the outer illuminators of the bore 258 may be controlled. The outer illuminators of the bore 258 are controlled in the same manner as the inner illuminators of the bore 258.

Figure 11:
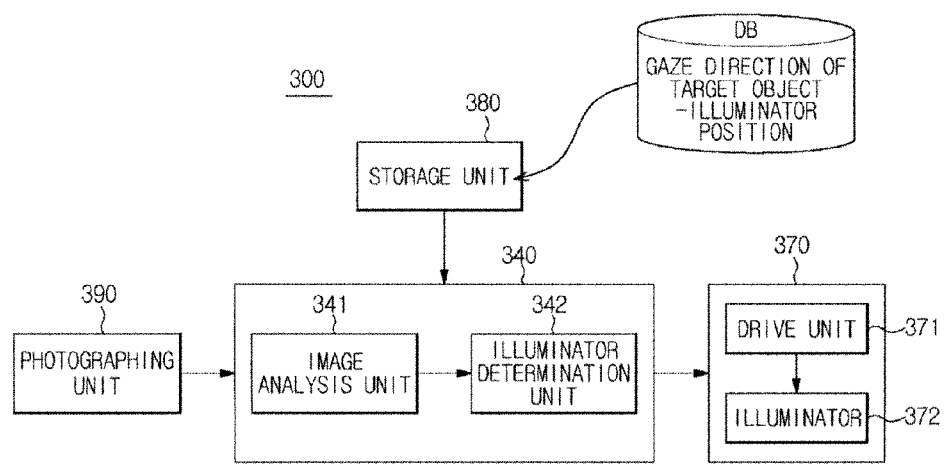
FIG. 11 is a control block diagram of a magnetic resonance imaging apparatus in accordance with principles of the present invention.

FIG. 11 shows a control block diagram of a magnetic resonance imaging apparatus 300 including a photographing unit 390 photographing an image of a patient, an illuminator unit 370 illuminating the inside of the bore, an illuminator control unit 340 confirming a gaze direction of the patient by analyzing the photographed image and controlling brightness of illuminators, and a storage unit 380 in which information regarding the positions of the illuminators is stored. The photographing unit 390 is a wide viewing angle camera acquiring a still image or moving images and transmits the acquired image to the image analysis unit 341. The still image may be acquired at a user configurable time interval. Further, the photographing unit 390 is installed above the position at which the head of the patient is located to enable confirmation of a gaze direction of the patient from the acquired image. Unit 390 also acquires a top view image of the inside of the bore.

The illuminator unit 370 includes illuminators 372 installed on the inner surface of the magnet assembly 350 and a drive unit 371 driving the illuminators 372, and the illuminators 372 may be formed in an array shape. Further, brightness of the illuminators 372 is adjustable, and the drive unit 371 receives a control signal from the illuminator control unit 340 and adjusts brightness or color of the illuminators 372. The image analysis unit 341 determines the current gaze direction of the patient by analyzing the photographed image as previously described. There are various known methods of recognizing a gaze direction of a person from a photographed image. For example, known methods include, tracking the positions of the pupils of a person in conjunction with tracking a degree of movement of the head of the person. In order to measure the degree of movement of the head of the person, a known method uses the position of a specific region, such as a nose or a mouth, and measures the rotation angle of the head of the person by matching a predetermined face model with the photographed face of the person.

Figure 12:
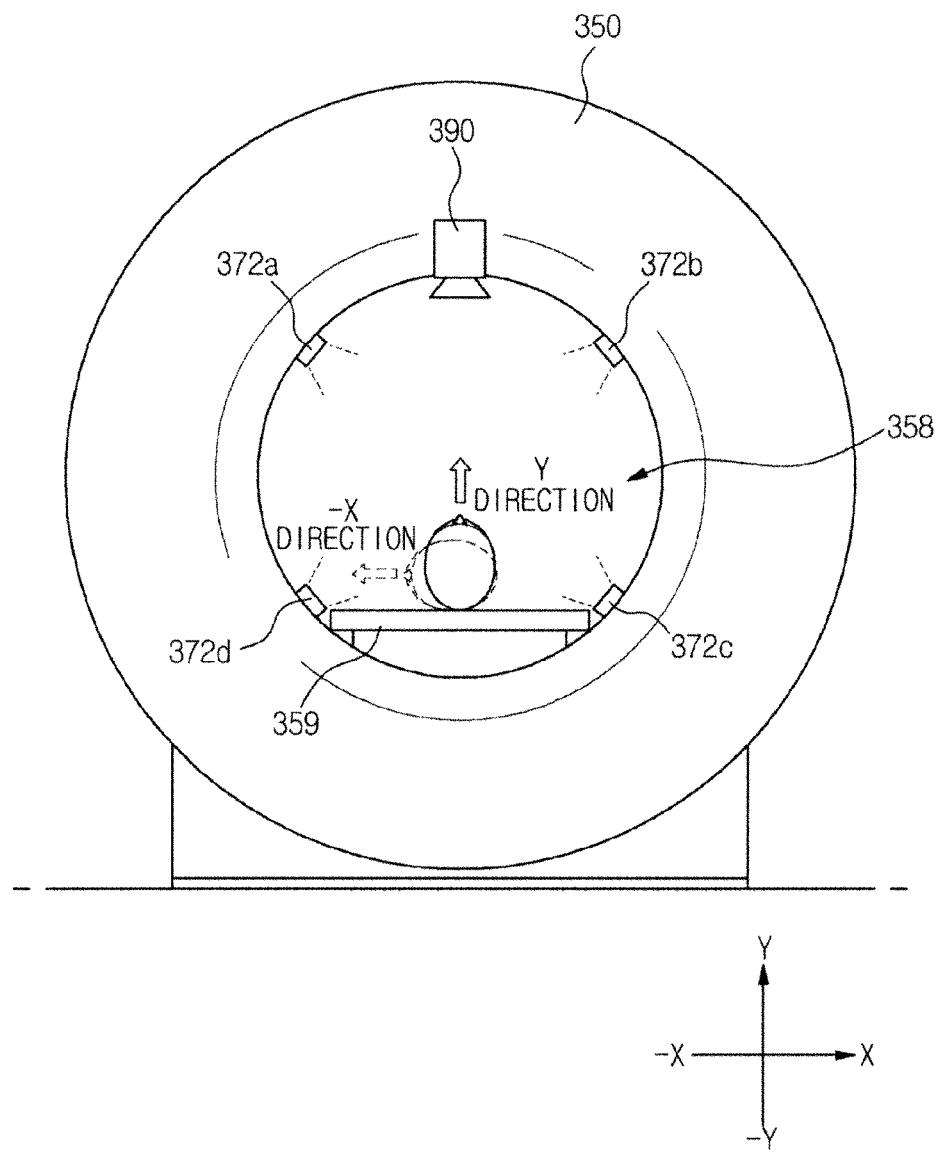
FIG. 12 is a view illustrating the operation of the magnetic resonance imaging apparatus in accordance with principles of the present invention.

The illuminator determination unit 342 decreases brightness of illuminators corresponding to the gaze direction of the patient. As shown in FIG. 12, illuminators 372a, 372b, 372c and 372d are installed on the inner surface of the magnet assembly 350 to illuminate the inside of the bore 358. Since the inner space of the bore 358 is narrow, the patient 20 on table 359 may suffer discomfort, such as glare, if brightness of the illuminators 372a, 372b, 372c and 372d is high. Therefore, the illuminator determination unit 342 decreases brightness of illuminators located in the gaze direction of the patient 20 so that the patient 20 does not suffer discomfort.

The illuminator determination unit 342 uses information stored in the storage unit 380 in determining brightness of the illuminators 372a, 372b, 372c and 372d. The storage unit 380 stores information regarding the illuminators 372a, 372b, 372c and 372d located at positions corresponding to the gaze directions of the patient. For example, when the patient 20 gazes in a designated direction, information identifying which of the illuminators may cause glare to the patient 20 among the four illuminators 372a, 372b, 372c and 372d is stored associated with the direction. When the illuminators 372a, 372b, 372c and 372d corresponding to the gaze directions of the patient are stored in the storage unit 380, the illuminator determination unit 342 decreases brightness of the illuminators corresponding to the gaze direction of the patient confirmed by the image analysis unit 341.

With reference to FIG. 12, if the gaze direction of the patient confirmed by the image analysis unit 341 is a −X direction, the illuminator determination unit 342 may decrease brightness of the illuminator 372d corresponding to such a direction, and if the gaze direction of the patient confirmed by the image analysis unit 341 is a Y direction, the illuminator determination unit 342 may decrease brightness of the illuminators 372a and 372b corresponding to such a direction. The brightness of the illuminators is adjusted to a level predetermined through experimentation, statistics or simulation in response to a distance between the patient and the illuminators to provide comfort.

Figure 13:
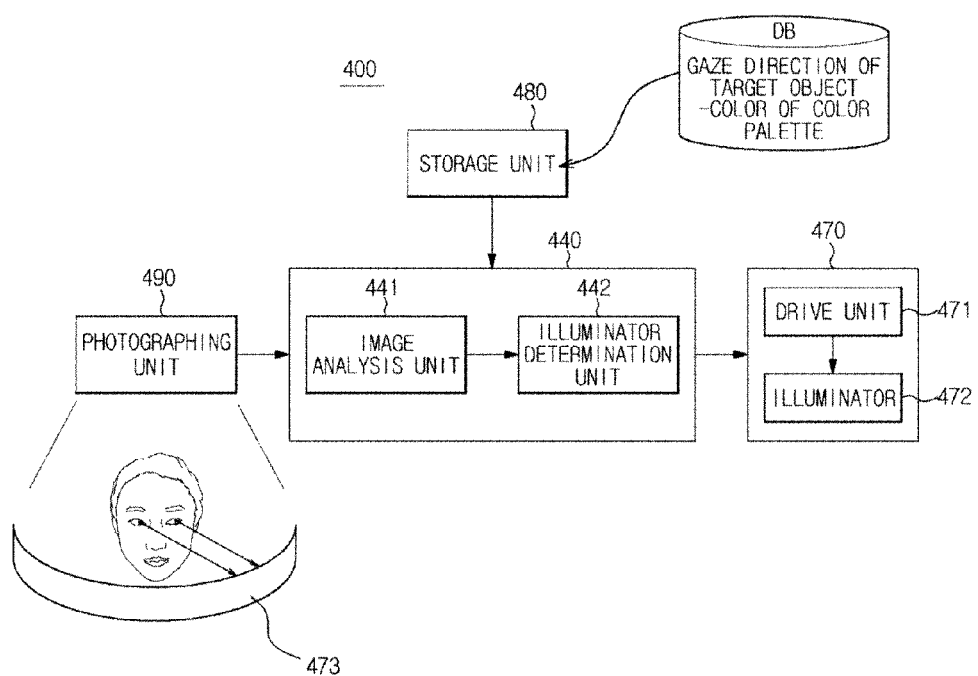
FIG. 13 is a control block diagram of a magnetic resonance imaging apparatus in accordance with principles of the present invention.

FIG. 13 is a control block diagram of a magnetic resonance imaging apparatus 400 including a color palette 473, an illuminator unit 470 illuminating the inside of a bore 458 and mounted on the inner surface of a magnet assembly 450 (FIG. 14), a photographing unit 490 photographing a patient on table 459, a storage unit 480 in which information regarding colors of the color palette 473 corresponding to gaze directions of the patient is stored, and an illuminator control unit 440 confirming a gaze direction of the patient from the acquired image of the patient and controlling an illuminator color and brightness using the information stored in the storage unit 480.

Figure 14A:
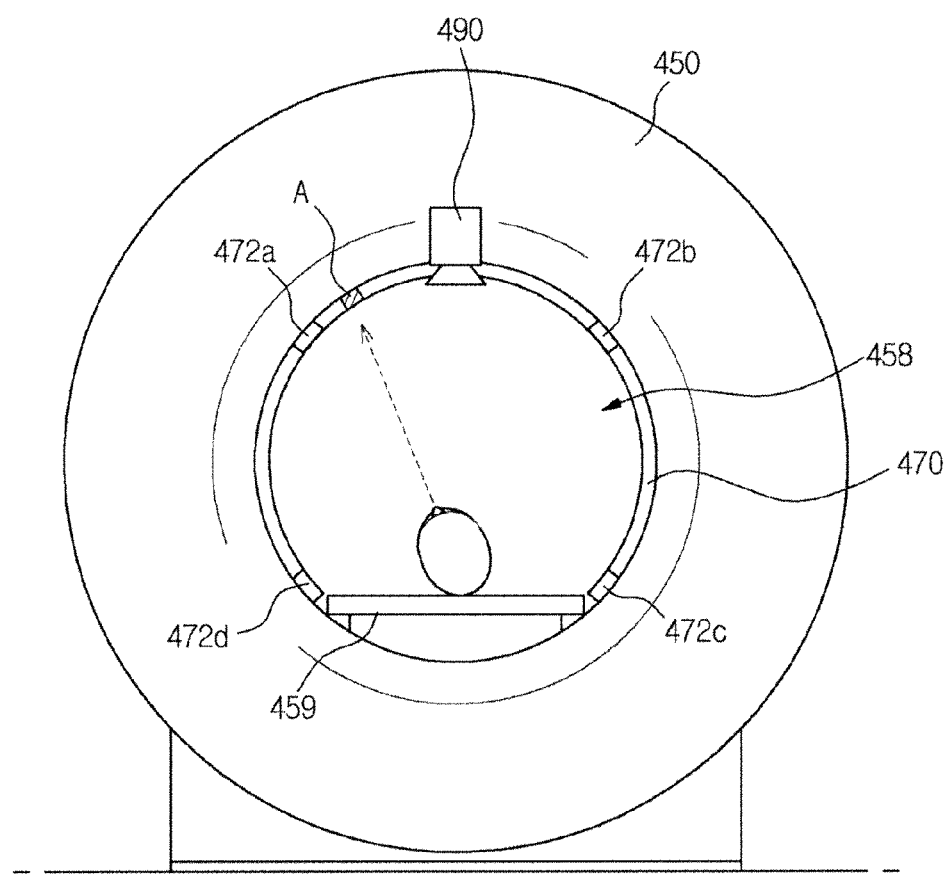
FIGS. 14A and 14B are views illustrating the external appearance of the magnetic resonance imaging apparatus in accordance with the embodiment of FIG. 13.
Figure 14B:
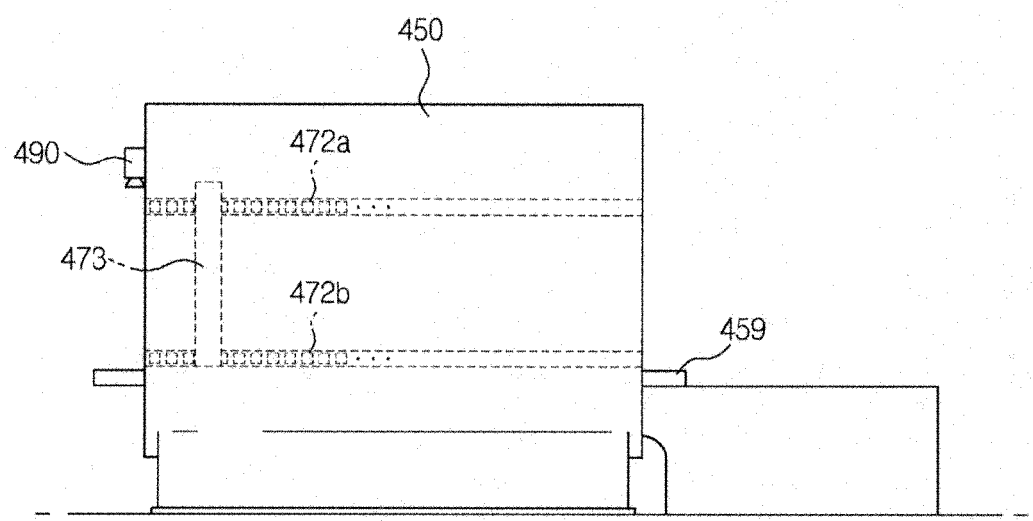

The photographing unit 490 is a wide viewing angle camera as previously described. The photographing unit 490 is mounted at the outside of the bore 458, as shown in FIGS. 14A and 14B, so as to eliminate effect of a magnetic field, and positioned above the head of the patient to determine the gaze direction of the patient from the acquired image, and photograph a top view image of the inside of the bore 458. The photographed image may be a moving image, or a still image acquired at a user designated time interval. The illuminator unit 470 includes illuminators 472 and a drive unit 471 driving the illuminators 472, and the illuminators 472 emit light of various colors. The illuminators 472 are LEDs unaffected by the magnetic field, comprising four LED arrays that uniformly illuminate the overall inside of the bore 458, as shown in FIGS. 14A and 14B.

Multiple different colors are arranged on the color palette 473. The color palette 473 may be provided by LEDs or may be a printed color palette. The number and kinds of colors arranged on the color palette 473 are not limited, but the illuminators 472 need to provide the colors arranged on the color palette 473. Further, the color palette 473 may be mounted on the inner surface of the magnet assembly 450, as shown in FIGS. 14A and 14B, so that the patient 20 lying in the bore 458 sees the color palette 473. The palette 473 may move along the vertical axis in response to the position of the head of the patient within the bore 458 and region of the patient to be photographed and the height of the patient.

The image analysis unit 441 determines the gaze direction of the patient 20 by analyzing the image acquired by the photographing unit 490 as previously described. The illuminator determination unit 442 determines a color of the color palette 473 corresponding to the gaze direction of the patient 20 determined by the image analysis unit 441 as the illuminator color. The information stored in the storage unit 480 may be used, and colors of the color palette 473 determined to be seen by the patient 20 based on the gaze direction of the patient 20 may be stored in the storage unit 480. Storage unit 480 stores a database associating gaze directions of the patient 20 with corresponding colors of the color palette 473 in response to a distance between the patient 20 and the color palette 473 and relative positions of the patient 20 and the color palette 473.

When the illuminator determination unit 442 transmits a control signal to the drive unit 471, the drive unit 471 changes the color of the illuminator 472 to the color determined by the illuminator determination unit 442. Thereby, the color of the illuminators 472a, 472b, 472c and 472d is changed to the color A of the color palette 473 which the patient 20 sees. This allows the patient to feel psychologically stable in a noisy and narrow environment. When the color of the illuminators 472a, 472b, 472c and 472d is changed to the color A of the color palette 473 which the patient 20 sees, the patient 20 may feel comfort in interaction with the magnetic resonance imaging apparatus 400. Further, in order to maximize such effects, the magnetic resonance imaging apparatus 400 controls illuminators on the outside of the bore 458 as well as the illuminators on the inside of the bore 458. Here, the outer illuminators of the bore 458 are illuminators of a scan room in which magnetic resonance imaging is carried out. The outer illuminators of the bore 458 are controlled in the same manner as the inner illuminators of the bore 458

Figure 15:
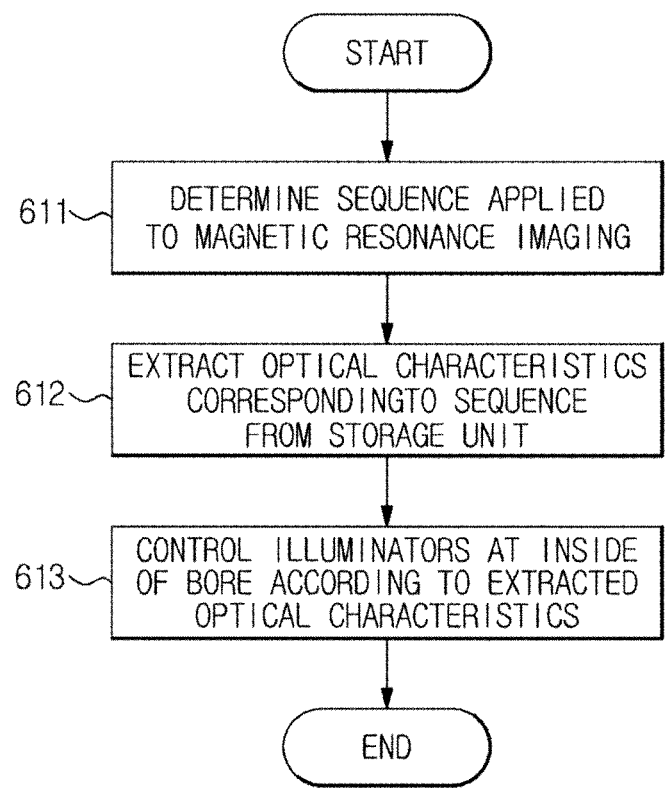
FIG. 15 is a flowchart illustrating a control method of a magnetic resonance imaging apparatus in accordance with principles of the present invention.

FIG. 15 shows a flowchart illustrating a control method of a magnetic resonance imaging apparatus. A scan sequence is used for magnetic resonance imaging and determined based on patient region to be imaged, an imaging method, or a diagnosis purpose (Operation 611). There are various scan sequences that may be applied to magnetic resonance imaging, such as sequences for diffusion tensor imaging (DTI), MR spectroscopy (MRS), functional MRI (fMRI), and diffusion weighted imaging (DWS) imaging, based on patient region to be imaged, imaging method to be used, and diagnosis purpose. Thereafter, optical characteristics corresponding to the scan sequence applied to magnetic resonance imaging are extracted from information stored in the storage unit, i.e., a database (Operation 612) such as, an illuminator color. For this purpose, a database associates illuminator colors with corresponding respective scan sequences is stored in the storage unit. The system selects, for example, a color exhibiting a high recognition time decreasing rate corresponding to a scan sequence having a long imaging time, and a color providing stability to a person (a color having high parasympathetic nervous activity) corresponding to a scan sequence sensitive to movement. The color exhibiting a high recognition time decreasing rate and the color providing stability may be determined through experimentation or statistically.

The system controls illuminator color in the bore in response to the extracted optical characteristics (Operation 613). If the extracted optical characteristics are illuminator color, the illuminator color in the bore is changed to the extracted illuminator color. For this purpose, the illuminators in the bore may include light sources which may vary the color of emitted light, i.e., the wavelength of emitted light. Further, in order to maximize such effects, the color of illuminators at the outside of the bore, i.e., the color of illuminators of a scan room, as well as the color of the illuminators at the inside of the bore may be controlled.

Figure 16:
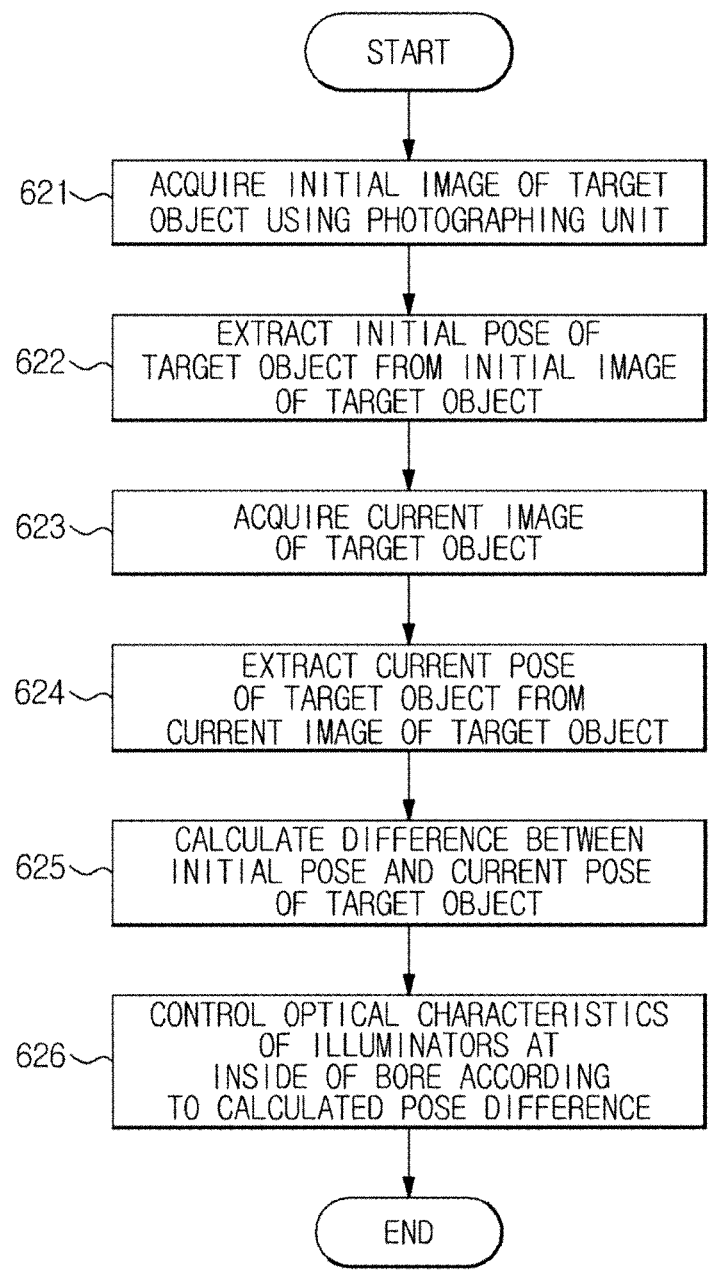
FIG. 16 is a flowchart illustrating a control method of a magnetic resonance imaging apparatus using movement of a target object in accordance with principles of the present invention.

FIG. 16 shows a flowchart illustrating a control method of a magnetic resonance imaging apparatus in response to movement of a patient. An initial image of the patient is acquired at the initial stage of magnetic resonance imaging using the photographing unit (Operation 621). Here, the image of the patient may be a moving image, or a still image. The photographing unit is installed at the outside of the bore to avoid magnetic field effects, and is a wide viewing angle camera to photograph an image representing movement of the patient. An initial pose of the patient is identified from the initial image of the patient (Operation 622) using a known boundary detection method as previously described, for example. A current image of the patient is acquired in real time or at a designated time interval (Operation 623), and a current pose of the patient is identified from the acquired current image (Operation 624).

In order to judge a degree of movement of the patient, a difference between the current pose and the initial pose of the patient is calculated by comparing the current pose of the patient with the initial pose of the patient (Operation 625). Optical characteristics of the illuminators on the inside of the bore are controlled based on the difference (Operation 626). For example, as the difference between the initial pose and the current pose of the patient increases, the system determines a degree of, movement of the patient increases, and a color providing stability to the patient is determined as the illuminator color from a database indicating illuminator colors associated with corresponding to degrees of movement of the patient. In order to maximize such effects, the color of illuminators at the outside of the bore, i.e., the color of illuminators of a scan room, as well as the color of the illuminators at the inside of the bore are similarly controlled.

Figure 17:
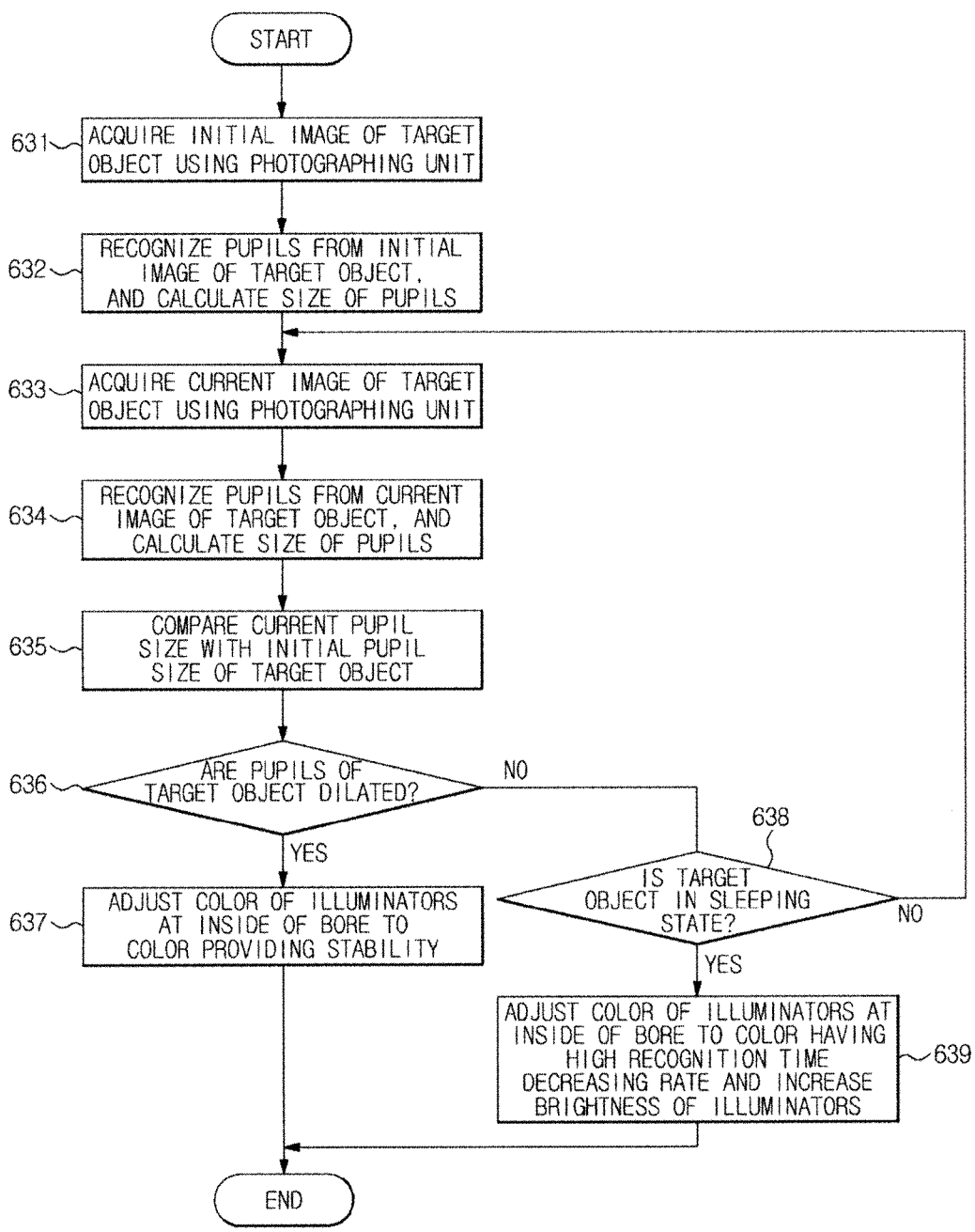
FIG. 17 is a flowchart illustrating a control method of a magnetic resonance imaging apparatus using recognition of pupils of a target object in accordance with principles of the present invention.

FIG. 17 shows a flowchart illustrating a control method of a magnetic resonance imaging apparatus using recognition of pupils of a patient. An initial image of the patient is acquired at the initial stage of magnetic resonance imaging using the photographing unit (Operation 631). Pupils of the patient are recognized from the initial image of the patient, and the size of the pupils is calculated (Operation 632). The calculated size becomes an initial pupil size of the patient. A current image of the patient is acquired in real time or at a user (or system) designated time interval (Operation 633), and pupils are recognized from the acquired current image and the size of the pupils is calculated (Operation 634). The calculated size becomes a current pupil size of the patient. The current pupil size of the patient is compared with the initial pupil size of the patient (Operation 635), and upon judging that the pupils of the patient are dilated (yes in Operation 636), the illuminator color in the bore is adjusted to a color providing stability (Operation 637). If the calculated current pupil size of the patient is below a designated reference value, i.e., upon judging that the patient is in a sleeping state or in a drowsy state (yes in Operation 638), the illuminator color in the bore is adjusted to a color exhibiting a high recognition time decreasing rate and brightness of the illuminator color is increased so that the patient does not fall asleep (Operation 639).

Figure 18:
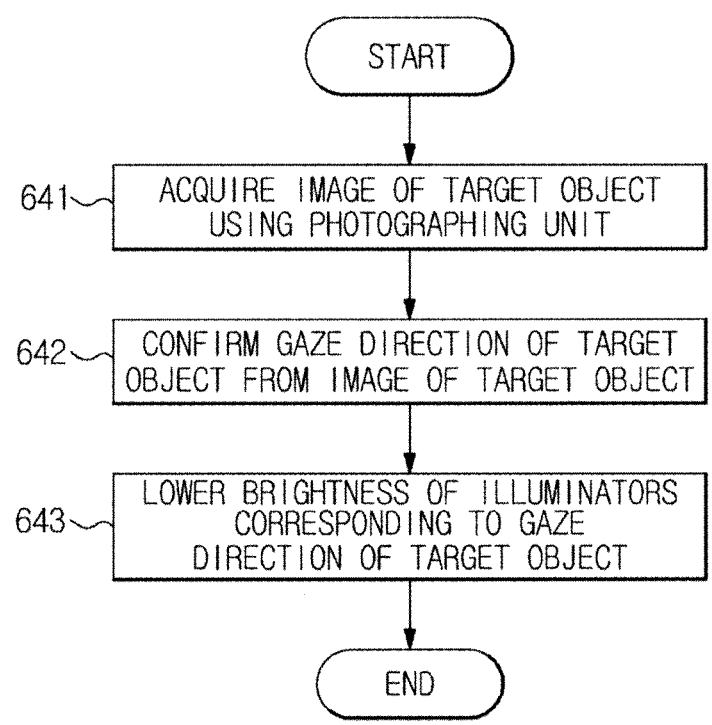
FIG. 18 is a flowchart illustrating a control method of a magnetic resonance imaging apparatus in accordance with principles of the present invention.

FIG. 18 shows a flowchart illustrating a control method of a magnetic resonance imaging apparatus. An image of a patient is acquired using the photographing unit (Operation 641). A gaze direction of the patient determined from the acquired image of the patient (Operation 642). In order to determine the gaze direction of the patient, one of a number of known image analysis methods may be used including, for example, a method in which the angle of the head of the patient and the positions of the pupils of the patient are calculated and the gaze direction of the patient is determined using results of calculation. Brightness of illuminators corresponding to the determined gaze direction of the patient is lowered (Operation 643). This prevents glare from disturbing the patient. Data indicating the positions of the illuminators corresponding to the gaze directions of the patient is stored in advance in the storage unit.

FIG. 19 shows a further flowchart illustrating a control method of a magnetic resonance imaging apparatus using a color palette 473 and an illuminator unit 470 mounted on the inner surface of a magnet assembly, various colors are arranged on the color palette 473, and the illuminator unit 470 selects and provides a color from the colors arranged on the color palette 473. An image of a patient is obtained using the photographing unit (Operation 651) and a gaze direction of the patient is determined from the acquired image of the patient (Operation 652) as previously described. A color of the color palette 473 corresponding to the gaze direction of the patient is identified from a storage unit 480 (Operation 653), and the illuminator color in the bore is adjusted to match the identified color of the color palette 473 (Operation 654). Colors of the color palette 473 corresponding to the gaze directions of the patient are stored in the storage unit 480. In more detail, a database in unit 480 associates gaze directions of the patient 20 with corresponding colors of the color palette 473 in response to a distance between the patient and the color palette 473 and relative positions of the patient and the color palette 473. This allows the patient to feel psychologically stable even in a noisy and narrow environment. When the illuminator color in the bore is changed to the color of the color palette 473 at which the patient directs his gaze, the patient is comforted by interaction with the magnetic resonance imaging apparatus. Further, in order to maximize such effects, illuminators at the outside of the bore as well as illuminators at the inside of the bore are similarly controlled. The outer illuminators of the bore comprise illuminators of a scan room in which magnetic resonance imaging is carried out. The outer illuminators of the bore are controlled similarly to the inner illuminators. In the system, color or brightness of illuminators at the inside of a bore is adjusted according to a scan sequence for magnetic resonance imaging or the state of a patient, thus easing discomfort of the patient during magnetic resonance imaging.

Although a few embodiments of the present invention have been shown and described, it would be appreciated by those skilled in the art that changes may be made in these embodiments without departing from the principles and spirit of the invention, the scope of which is defined in the claims and their equivalents.

The above-described methods according to the present invention can be implemented in hardware, firmware or as software or computer code that can be stored in a recording medium such as a CD ROM, an RAM, a floppy disk, a hard disk, or a magneto-optical disk or computer code downloaded over a network originally stored on a remote recording medium or a non-transitory machine readable medium and to be stored on a local recording medium, so that the methods described herein can be rendered in such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein.

What is claimed is:

1. A magnetic resonance imaging (MRI) apparatus comprising:
a magnet assembly having a bore for accommodating a patient;
a main control unit for controlling operation of the magnet assembly during performance of an MRI procedure;
illuminators installed on the inside of the bore;
a storage unit for storing a database of information regarding illumination colors associated with corresponding different scan sequences usable during the MRI procedure, with each scan sequence corresponding to: (i) an illumination color associated with a human recognition time which is correlated with a length of imaging time of that scan sequence; or (ii) an illumination color associated with a stability value which is correlated with movement sensitivity for that scan sequence, or a combination thereof; and
an illuminator control unit that receives information from the main control unit regarding a scan sequence to be used during the MRI procedure, determines an output illumination color corresponding to the scan sequence to be used from the database of information in the storage unit, and controls optical characteristics of the illuminators to generate the output illumination color during the MRI procedure.

2. The magnetic resonance imaging apparatus according to claim 1, wherein the database of information includes, for a particular scan sequence of the different scan sequences, at least an illumination color associated with the human recognition time which is correlated with the length of imaging time of the particular scan sequence.

3. The magnetic resonance imaging apparatus according to claim 1, wherein the database of information includes, for a particular scan sequence of the different scan sequences, at least an illumination color associated with a stability value which is correlated with movement sensitivity for the particular scan sequence, for providing stability to the patient.

4. The magnetic resonance imaging apparatus according to claim 1, wherein the storage unit further stores information regarding optical characteristics of the illuminators corresponding to scan sequences,
wherein the illuminator control unit controls the optical characteristics of the illuminators using the information regarding optical characteristics stored in the storage unit.

5. A magnetic resonance imaging (MRI) apparatus comprising a magnet assembly and a bore for accommodating a patient, comprising:
- a photographing unit configured for acquiring an image of a patient in the bore, and installed on the outside of the bore;
- an illuminator unit installed on the inside of the bore; and
- an illuminator control unit determining a state of the patient including at least one of an eye pupil state of the patient, a facial expression of the patient, gaze direction of the patient, and a movement of the patient, by analyzing the image acquired by the photographing unit, and controlling optical characteristics of illuminators comprised in the illuminator unit to set an illumination color or brightness during an MRI procedure that provides stability, reduces discomfort, or awakens the patient, in accordance with the determined state of the patient.

6. The magnetic resonance imaging apparatus according to claim 5, wherein the image of the patient is a moving image or a still image photographed at a designated time interval.

7. The magnetic resonance imaging apparatus according to claim 6, wherein the photographing unit includes a wide viewing angle camera, and photographs a top view image of an inside of the bore.

8. The magnetic resonance imaging apparatus according to claim 6, wherein the illuminator control unit determines whether or not the patient moves by analyzing the acquired images.

9. The magnetic resonance imaging apparatus according to claim 8, wherein the illuminator control unit adjusts the color of the illuminators to a color supporting patient stability, upon determining that the patient moves.

10. The magnetic resonance imaging apparatus according to claim 9, wherein the illuminator control unit varies the color of the illuminators according to degrees of movement of the patient.

11. The magnetic resonance imaging apparatus according to claim 10, further comprising a storage unit that stores data associating colors of the illuminators with corresponding degrees of movement of the patient,
- wherein the illuminator control unit controls the color of the illuminators using the data stored in the storage unit.

12. The magnetic resonance imaging apparatus according to claim 6, wherein the illuminator control unit recognizes pupils of the patient from the acquired image.

13. The magnetic resonance imaging apparatus according to claim 12, wherein the illuminator control unit compares a current pupil size of the patient with a pupil size of the patient at an initial stage of magnetic resonance imaging acquired images.

14. The magnetic resonance imaging apparatus according to claim 13, wherein, if the current pupil size of the patient is greater than the pupil size of the patient at the initial stage of magnetic resonance imaging, the illuminator control unit adjusts the color of the illuminators to a color providing stability to the patient.

15. The magnetic resonance imaging apparatus according to claim 12, wherein, if the pupils of the patient are not recognized as normal from the acquired image, the illuminator control unit adjusts the color of the illuminators to a color representing a short recognition time and increases brightness of the illuminators.

16. The magnetic resonance imaging apparatus according to claim 6, wherein the illuminator control unit recognizes a facial expression of the patient from the acquired image.

17. The magnetic resonance imaging apparatus according to claim 16, wherein the illuminator control unit adjusts the color of the illuminators to a color corresponding to a recognized facial expression of the patient.

18. The magnetic resonance imaging apparatus according to claim 6, wherein the illuminator control unit determines the gaze direction of the patient from the acquired image.

19. The magnetic resonance imaging apparatus according to claim 18, wherein the illuminator control unit decreases brightness of illuminators corresponding to the determined gaze direction.

20. The magnetic resonance imaging apparatus according to claim 6, further comprising a color palette comprising a plurality of arranged colors installed on the inside of the bore.

21. The magnetic resonance imaging apparatus according to claim 20, wherein the illuminator control unit determines a gaze direction of the patient by analyzing the acquired image, and adjusts the color of the illuminators to a color of the color palette corresponding to the gaze direction of the patient.

22. The magnetic resonance imaging apparatus according to claim 21, further comprising a storage unit storing information associating colors of the color palette with corresponding gaze directions of the patient,
- wherein the illuminator control unit controls the color of the illuminators using the information stored in the storage unit.

23. A control method in a magnetic resonance imaging (MRI) apparatus comprising a magnet assembly, a bore for accommodating a patient including illuminators installed on the inside of the bore, and at least one control unit, the control method performed by the at least one control unit and comprising:
- determining a scan sequence to be employed in an MRI procedure;
- determining an output illumination color corresponding to the scan sequence from a database of information stored in a storage unit of the MRI apparatus, wherein the information includes illumination colors associated with corresponding different scan sequences usable during the MRI procedure, with each scan sequence corresponding to: (i) an illumination color associated with human recognition time which is correlated with a length of imaging time of that scan sequence, or (ii) an illumination color associated with a stability value which is correlated with movement sensitivity for that scan sequence, or a combination thereof, and
- performing the MRI procedure and controlling the illuminators to provide the output illumination color corresponding to the scan sequence during the MRI procedure.

24. The control method according to claim 23, wherein the database of information includes at least an illuminator color representing a short recognition time associated with a corresponding scan sequence requiring a long time for magnetic resonance imaging.

25. The control method according to claim 24, wherein the database of information includes at least an illumination color providing stability to a patient associated with a corresponding scan sequence sensitive to movement of the patient.

26. A control method in a magnetic resonance imaging apparatus comprising a magnet assembly and a bore for accommodating a patient including illuminators installed on the inside of the bore, the control method comprising:

acquiring, by a camera installed on the outside of the bore, an image of a patient in the bore;

determining, by at least one processor, a state of the patient including at least one of an eye pupil state of the patient, a facial expression of the patient, a gaze direction of the patient, and a movement of the patient, by analyzing the acquired image; and controlling, by the at least one processor, optical characteristics of the illuminators to set an illumination color or brightness during an MRI procedure that provides stability, reduces discomfort, or awakens the patient, in accordance with the determined state of the patient.

27. The control method according to claim 26, wherein the determination of the state of the patient includes determining whether or not the patient moves.

28. The control method according to claim 27, wherein the control of the optical characteristics of the illuminators includes adjusting the color of the illuminators to a color providing stability to the patient, upon determining that the patient moves.

29. The control method according to claim 26, wherein the determining of the state of the patient includes determining whether or not pupils of the patient are recognized from the acquired image or whether or not the pupils of the patient are dilated from the acquired image.

30. The control method according to claim 29, wherein the control of the optical characteristics of the illuminators includes, if the pupils of the patient are not recognized, adjusting the color of the illuminators to a color representing a short recognition time and increasing brightness of the illuminators.

31. The control method according to claim 29, wherein the control of the optical characteristics of the illuminators includes, if the pupils of the patient are dilated, adjusting the color of the illuminators to a color providing stability to the patient.

32. The control method according to claim 26, wherein the determination of the state of the patient includes determining the gaze direction of the patient.

33. The control method according to claim 32, wherein the control of the optical characteristics of the illuminators includes decreasing brightness of illuminators corresponding to the determined gaze direction.

34. The control method according to claim 26, wherein the determining of the state of the patient includes determining which color a patient is looking at of a plurality of colors arranged on a color palette.

35. The control method according to claim 34, wherein the control of the optical characteristics of the illuminators includes adjusting the color of the illuminators to the color of the color palette at which a patient gazes.

* * * * *